United States Patent
Ahmed

(10) Patent No.: US 10,195,424 B2
(45) Date of Patent: Feb. 5, 2019

(54) METHODS AND SYSTEMS FOR TREATMENT OF SPINAL DISORDERS USING TRANS-SPINAL DIRECT CURRENT STIMULATION

(71) Applicant: Zaghloul Ahmed, Staten Island, NY (US)

(72) Inventor: Zaghloul Ahmed, Staten Island, NY (US)

(73) Assignee: THE RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 236 days.

(21) Appl. No.: 14/930,303

(22) Filed: Nov. 2, 2015

(65) Prior Publication Data

US 2016/0243353 A1    Aug. 25, 2016

Related U.S. Application Data

(60) Provisional application No. 62/118,812, filed on Feb. 20, 2015, provisional application No. 62/126,021, filed on Feb. 27, 2015, provisional application No. 62/242,635, filed on Oct. 16, 2015.

(51) Int. Cl.
*A61N 1/36* (2006.01)
*A61N 1/20* (2006.01)
*A61N 1/04* (2006.01)

(52) U.S. Cl.
CPC ........... *A61N 1/205* (2013.01); *A61N 1/0456* (2013.01); *A61N 1/36014* (2013.01); *A61N 1/0468* (2013.01); *A61N 1/0476* (2013.01); *A61N 1/36121* (2013.01)

(58) Field of Classification Search
CPC .. A61N 1/205; A61N 1/0456; A61N 1/36014; A61N 1/36121; A61N 1/0476; A61N 1/0468
See application file for complete search history.

(56) References Cited

U.S. PATENT DOCUMENTS

| | | | |
|---|---|---|---|
| 4,919,140 A | 4/1990 | Borgens et al. | |
| 8,380,304 B2 | 2/2013 | Lozano | |
| 2005/0119712 A1 | 6/2005 | Shafer | |
| 2010/0274305 A1 | 10/2010 | Gliner et al. | |
| 2013/0035745 A1* | 2/2013 | Ahmed | A61N 1/0452 607/66 |

(Continued)

OTHER PUBLICATIONS

International Preliminary Report on Patentability and Written Opinion for international application No. PCT/US16/18167 dated Sep. 1, 2017.

(Continued)

*Primary Examiner* — Rex R Holmes
(74) *Attorney, Agent, or Firm* — Burns & Levinson LLP; Orlando Lopez; Janine M. Susan

(57) ABSTRACT

Methods, systems and devices are disclosed for treating a spinal disorder by applying a source of direct current to a spinal cord in animals, including humans. Trans-spinal direct current stimulation (tsDCS) uses direct current via cathodal and/or anodal stimulation to induce cell proliferation, cell differentiation, and/or cell migration at or near the area of the spinal cord being treated, and up-regulates or down-regulates protein expression by cells at or near the area of the spinal cord being treated.

31 Claims, 19 Drawing Sheets

(56) References Cited

U.S. PATENT DOCUMENTS

2013/0053922 A1* 2/2013 Ahmed .............. A61N 1/36003
607/45
2013/0090542 A1 4/2013 Kipke et al.

OTHER PUBLICATIONS

International Search Report and the Written Opinion dated May 2, 2016 for PCT/US2016/018167.
Ahmed, "Trans-Spinal Direct Current Stimulation Alters Muscle Tone in Mice with and without Spinal Cord Injury with Spasticity", The Journal of Neuroscience, Jan. 29, 2014, 34(5)1701-1709.
Gifondorwa et al., "Exogenous Delivery of Heat Shock Protein 70 Increases Lifespan in a Mouse Model of Amyotrophic Lateral Sclerosis", The Journal of Neuroscience, Nov. 28, 2007, 27(48):13173-13180.
Robinson et al., "Extracellular Heat Shock Protein 70: A Critical Component for Motoneuron Survival", The Journal of Neuroscience, Oct. 19, 2005, 25(42):9735-9745.
Keuters et al., "Transcranial Direct Current Stimulation Promotes the Mobility of Engrafted NSCs in the Rat Brain", NMR Biomed., 2015, 28:231-239.
McKenzie et al., "Motor Skill Learning Requires Active Central Myelination", Science, Oct. 17, 2014, vol. 346, Issue 6207, pp. 318-321.

\* cited by examiner

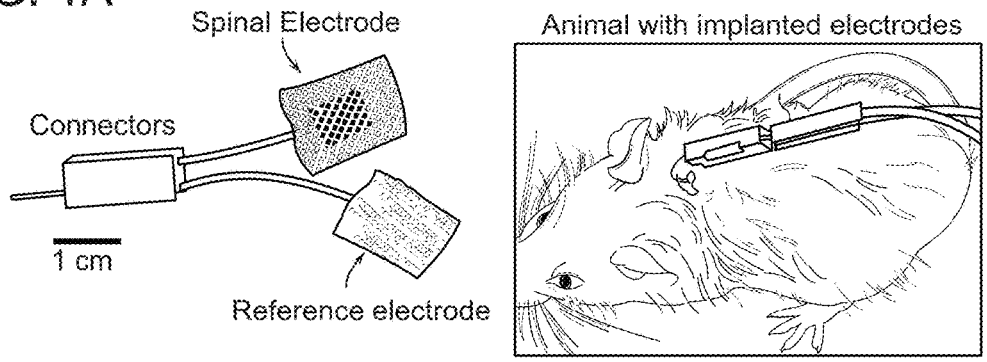
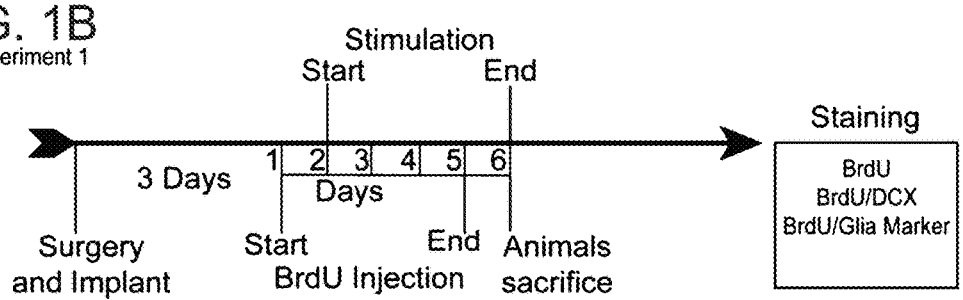
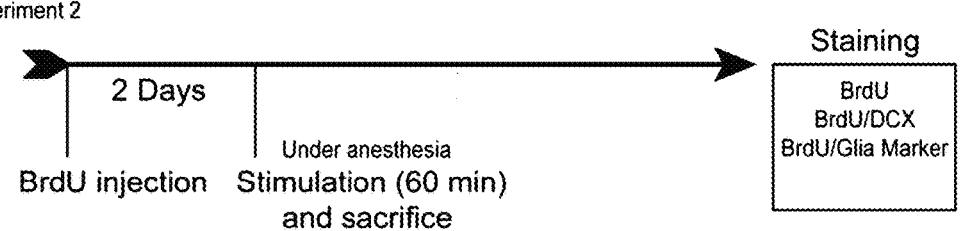
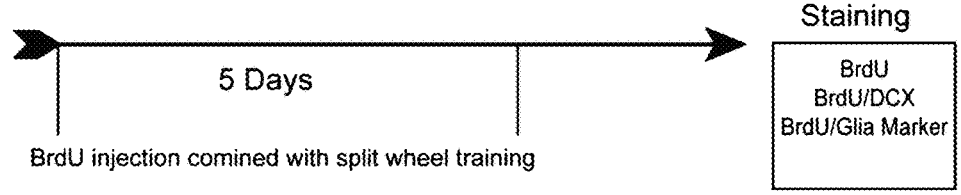
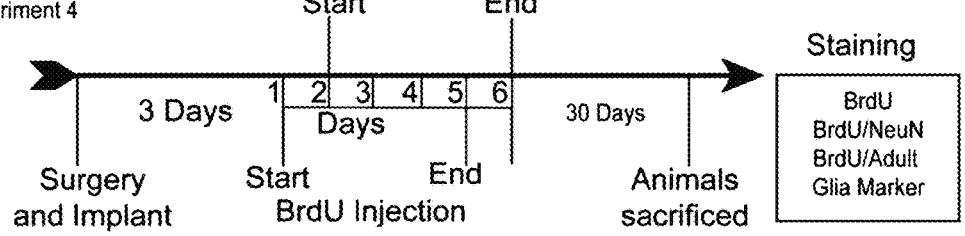

FIG. 3A
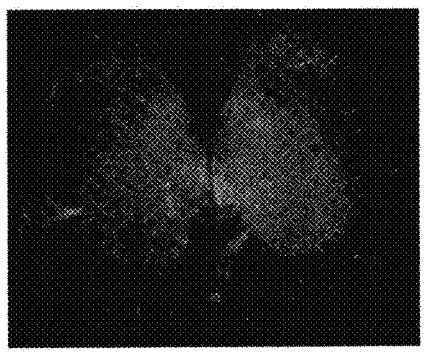 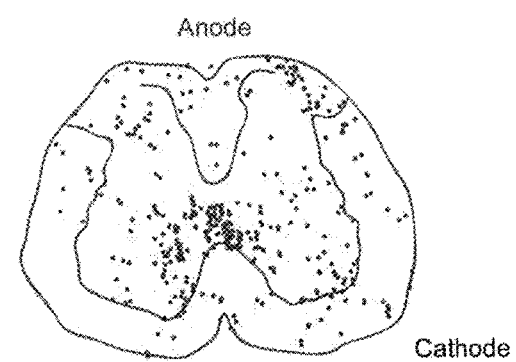
FIG. 3B
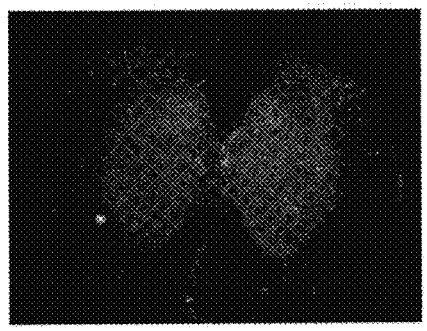 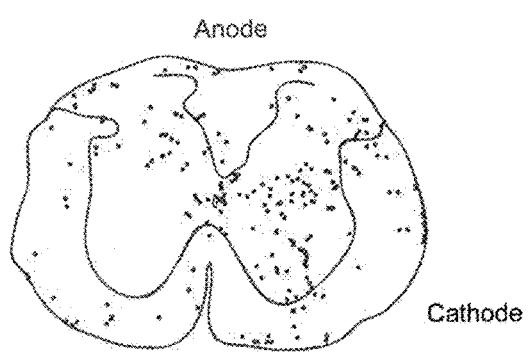
FIG. 3C
 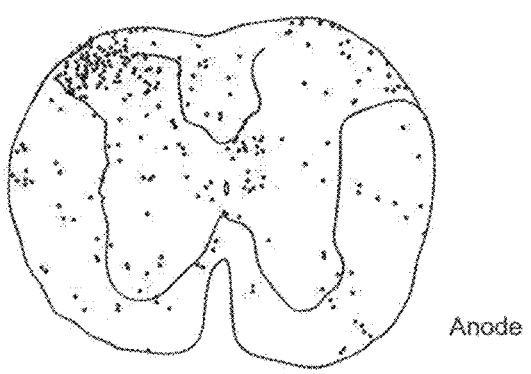

Sham-control

Cathodal stimulation
5 animals

Anodal stimulation
1 animal

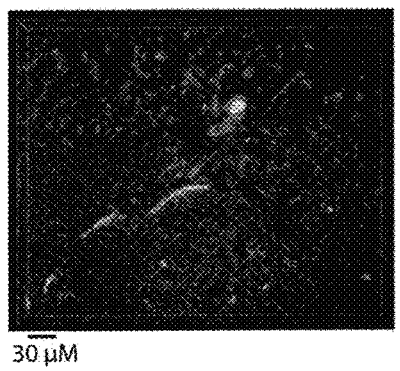
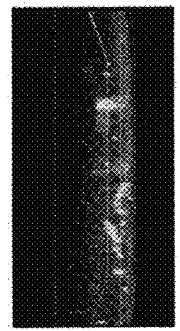
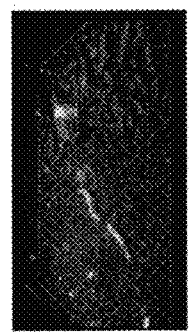
FIG. 7A　　　　FIG. 7B　　　　FIG. 7C　　　　FIG. 7D
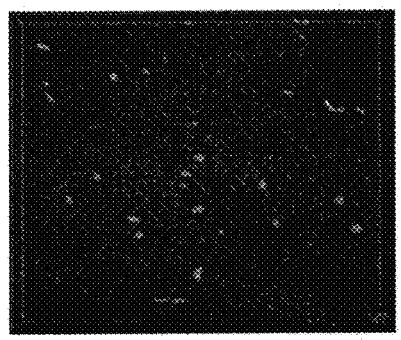
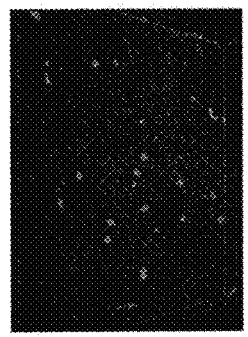
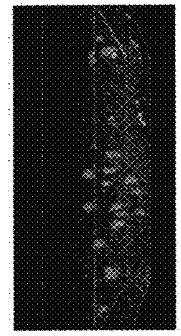
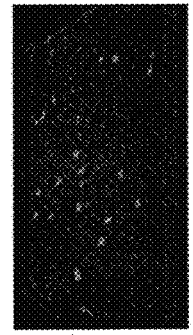
FIG. 7E　　　　FIG. 7F　　　　FIG. 7G　　　　FIG. 7H
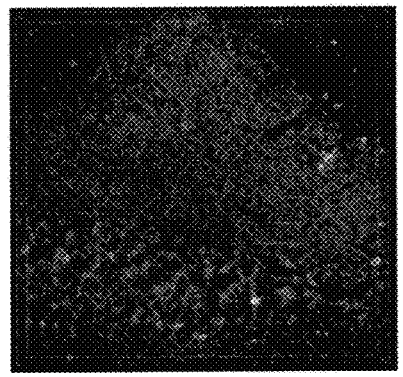
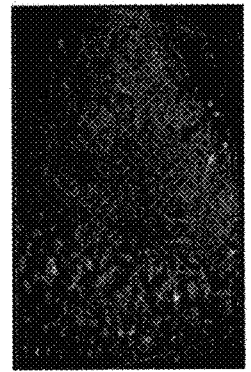
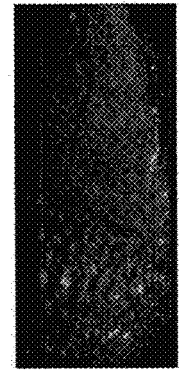
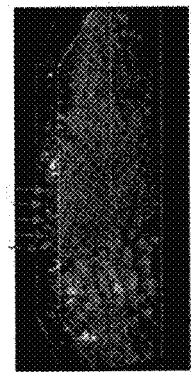
FIG. 7I　　　　FIG. 7J　　　　FIG. 7K　　　　FIG. 7L

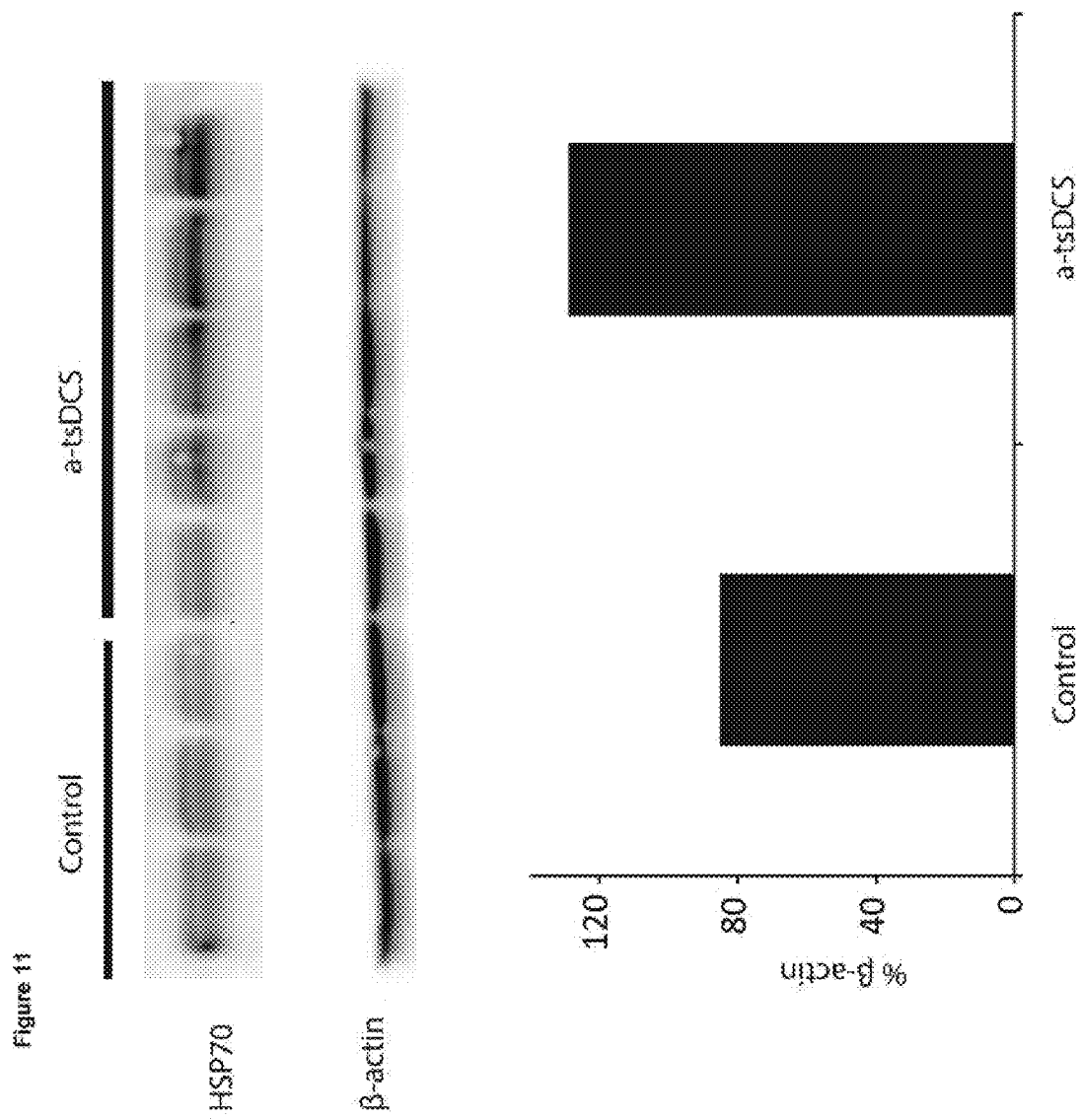

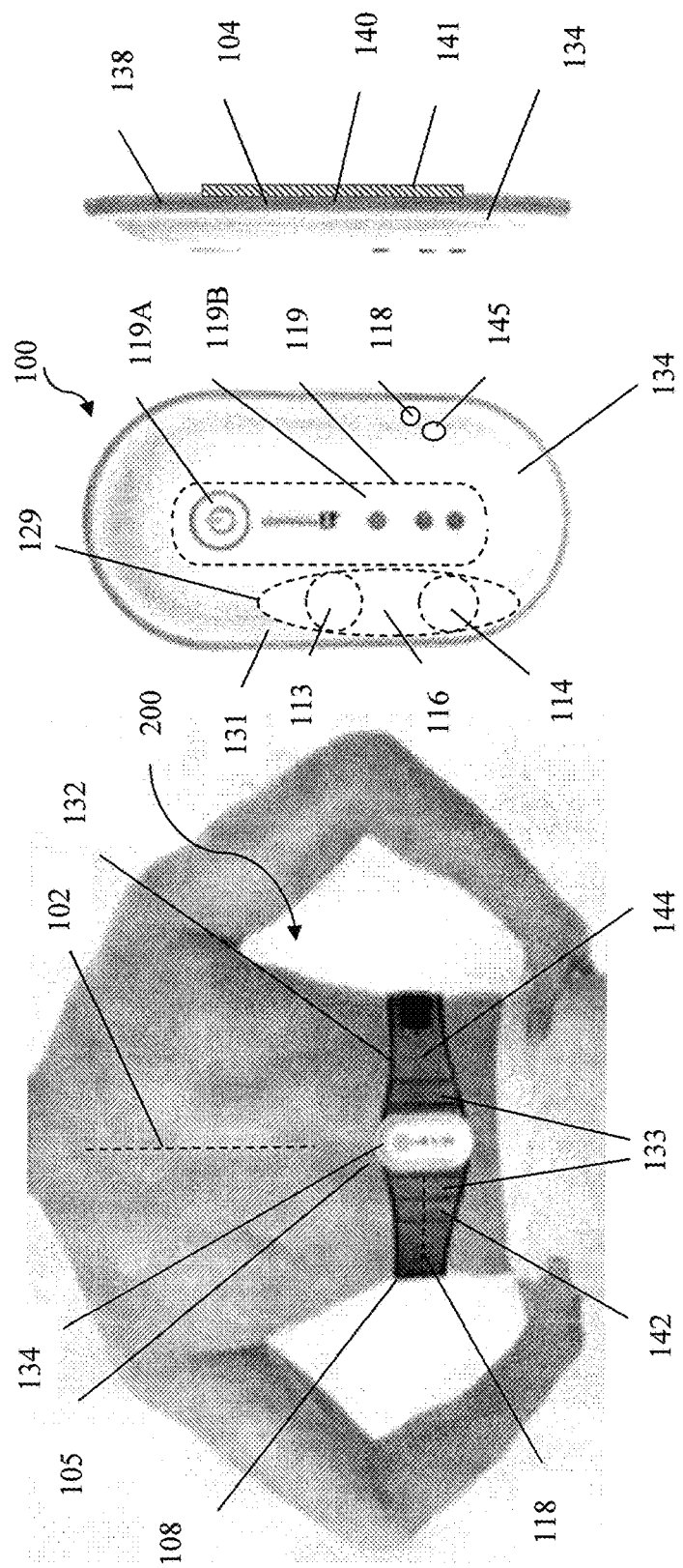

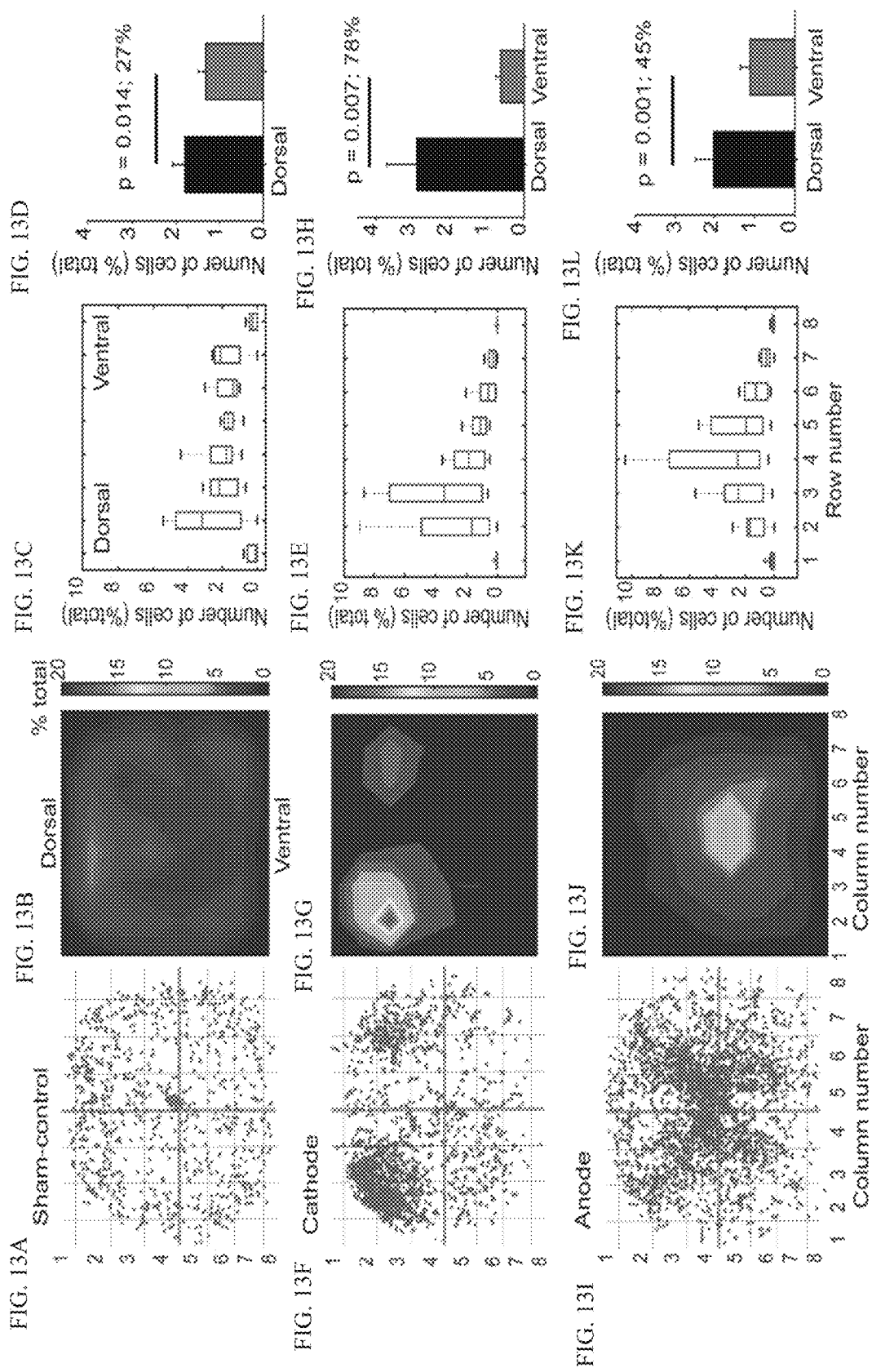

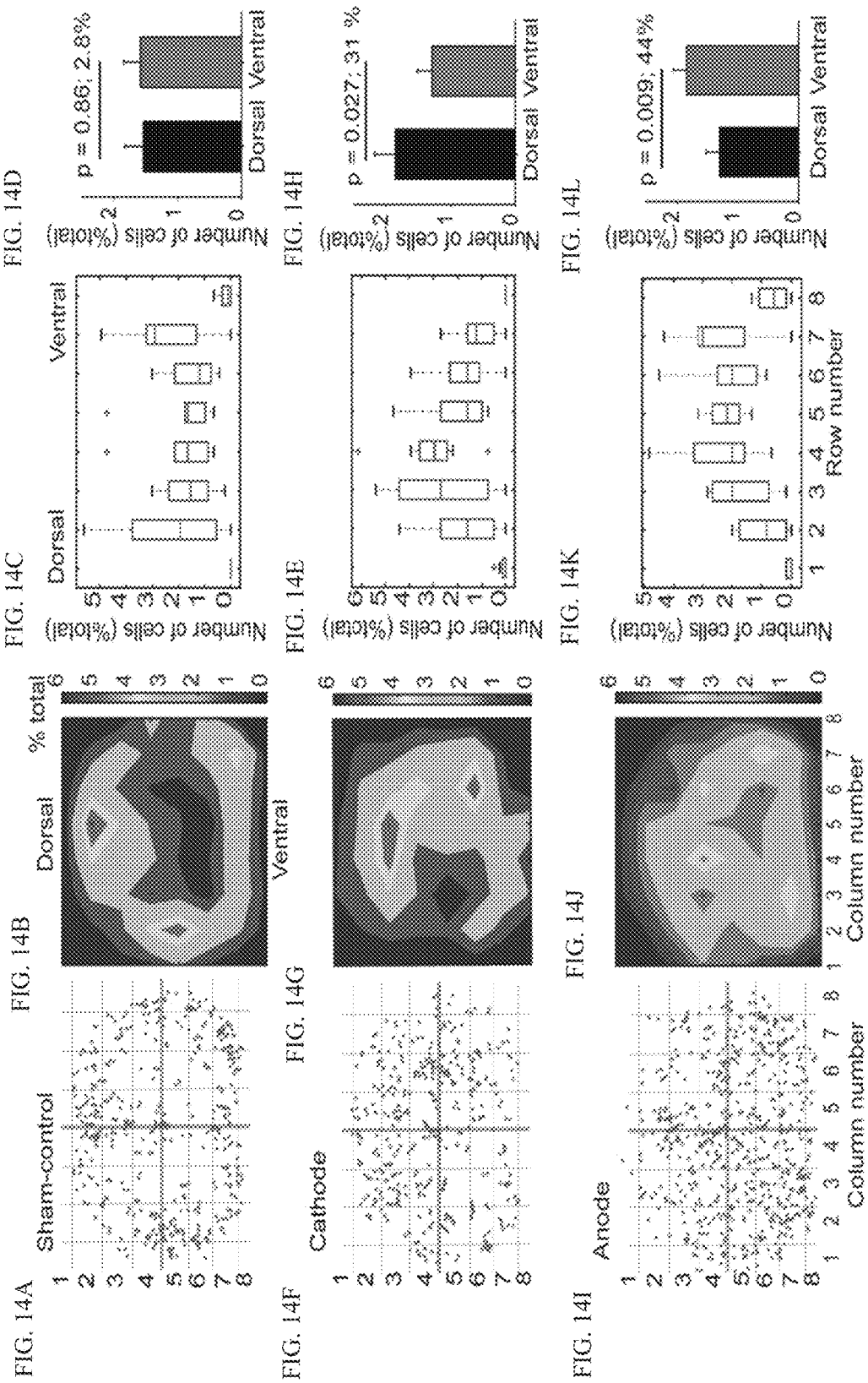

FIG. 15A
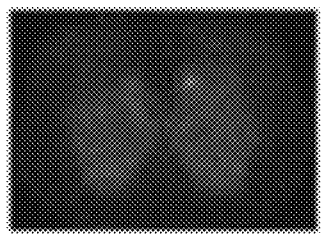 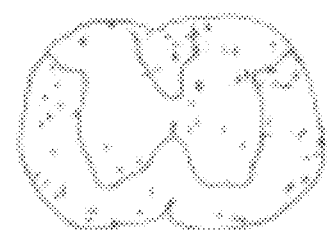
Sham-control
FIG. 15B
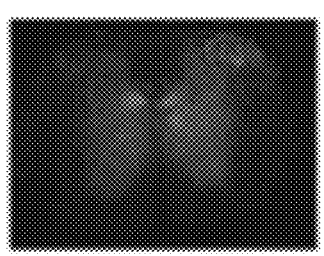 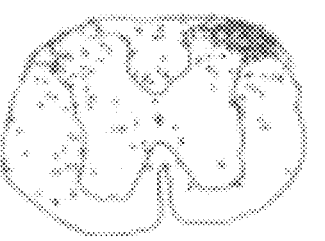
Cathode
FIG. 15C
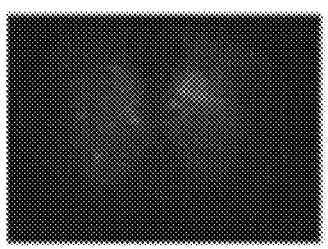 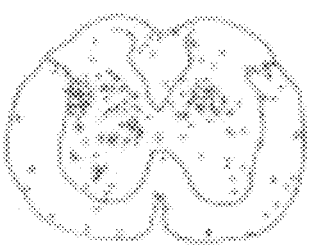
Anode
FIG. 15D
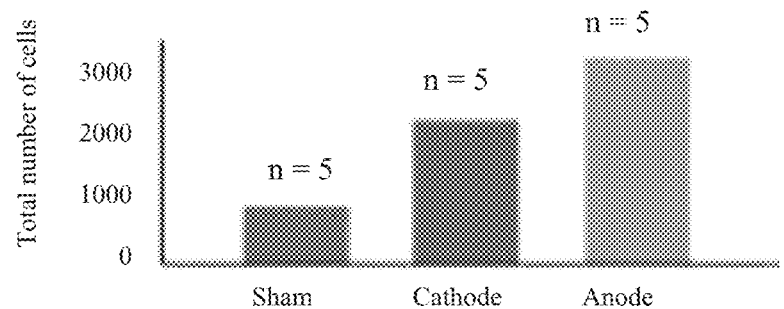

FIG. 17A  FIG. 17B  FIG. 17C  FIG. 17D
negative 2.5X  positive 2.5 X  negative 10 X  positive 10 X
   
FIG. 17E
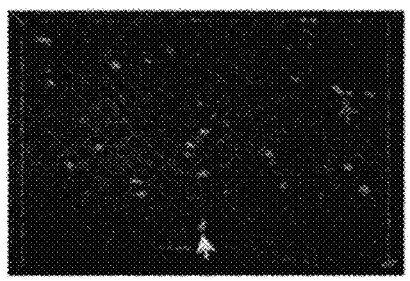 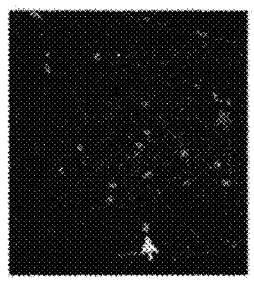 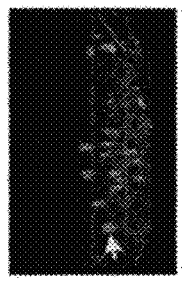 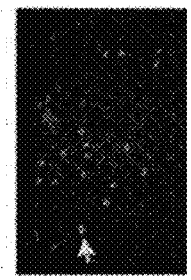
FIG. 17F
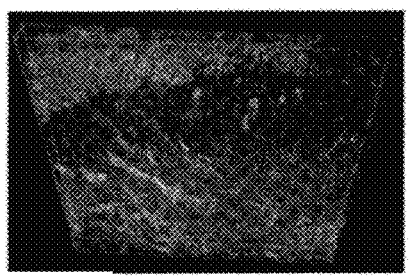 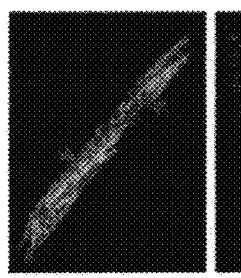  
FIG. 17G
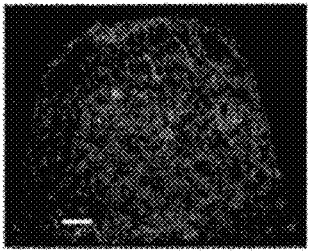 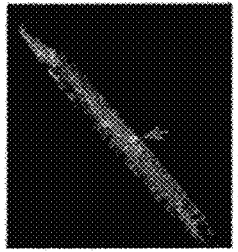 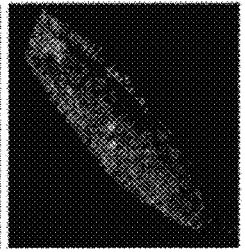 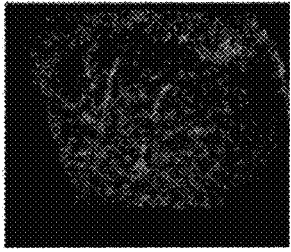

BDNF

NGF

METHODS AND SYSTEMS FOR TREATMENT OF SPINAL DISORDERS USING TRANS-SPINAL DIRECT CURRENT STIMULATION

CROSS-REFERENCE TO RELATED APPLICATIONS

This application claims the benefit of and priority to U.S. Provisional Application No. 62/118,812, filed Feb. 20, 2015; U.S. Provisional Application No. 62/126,021, filed Feb. 27, 2015; and U.S. Provisional Application No. 62/242,635, filed Oct. 16, 2015. All of the foregoing are incorporated herein by reference in their entirety for all purposes.

BACKGROUND

The spinal cord is vulnerable to a variety of injuries and disorders that can either be compressive, vascular, inflammatory, infectious, metabolic, genetic or developmental in nature. Some of the conditions that can affect the spinal cord include post-traumatic compression or disruption by fractured or displaced vertebra, disk herniation, cervical spondylosis, arteriovenous malformation, hemorrhage, multiple sclerosis, neuromyelitis optica, tranverse myelitis, Sjogren-related myelopathy, systemic lupus erythematosus, syringomyelia, meningomyelocele, tethered cord syndrome, vitamin B12 deficiency, amyotrophic lateral sclerosis, hereditary spastic paraparesis, spinal muscular atrophy and tropical spastic paraparesis/HTLV-1-associated myelopathy. Such conditions can result in motor, autonomic and/or sensory impairments. In some cases, surgical treatment or pharmacological therapy can treat the underlying cause of the spinal dysfunction, but in many cases no effective therapeutic interventions exist. The use of electrical stimulation for the treatment of spinal cord conditions has primarily focused on using implantable spinal cord stimulators for treating pain, and application to functional impairments are at an earlier stage of development. Implantable stimulators deliver stimulation signals to specific areas of the spinal cord, but require surgical implantation and precise electrode positioning. A need exists to treat spinal disorders and traumas and as patients with spinal disorders can benefit from non-invasive methods, systems and devices, the present invention provides these and other advantages as will be apparent from the following detailed description and accompanying figures.

SUMMARY OF THE INVENTION

In one or more embodiments, the present invention is directed to methods, systems and devices for treating a spinal disorder by applying a source of direct current to a spinal cord in animals, including humans and other sentient beings.

In one or more other embodiments, the methods, systems and devices of the invention are applied to treatment of spinal cord disorders or trauma using cathodal or anodal stimulation or alternating cathodal and anodal stimulation at the dorsal aspect of the spinal cord to increase the number of proliferating cells at or near the site of injury or other spinal location, and to promote differentiation of neuronal cells.

In one or more embodiments, the method of these teachings for treating a spinal cord condition in a vertebrate being includes applying at least one of cathodal or anodal stimulation at the dorsal aspect of the spinal cord in the area of a site of the condition to regulate biological activity of at least one of protein expression level or cell behavior in the area of the site. The stimulation is applied as constant direct current at an intensity and for a period of time sufficient to cause the biological activity to include at least one of proliferation, differentiation, migration or expression in the area of the site.

In one or more instances, the constant direct current is applied by a first electrode to the area of a dorsal aspect of the spinal cord and a second electrode is applied to the vertebrate being at a position remote from the dorsal aspect of the spinal cord, and the electrodes are oppositely charged.

In one or more instances, the first electrode is placed at or proximate to the location of the spinal cord condition and the constant direct current between the electrodes causes neural cells at or proximate to the spinal cord condition to at least one of migrate, proliferate or differentiate.

In one or more instances, the first electrode is a negatively charged electrode or a positively charged electrode.

In one or more instances, the spinal cord condition is a spinal cord injury and the constant direct current causes neural cells at the spinal cord to migrate toward the spinal cord injury. In one or more instances, the neural cells are neural stem cells.

In one or more instances, the constant direct current between the electrodes causes neural cells at or proximate to the location of the spinal cord condition to differentially express at least one of BDNF, NGF or HSP70.

In one or more instances, the method of these teachings for treating a spinal cord condition in a vertebrate being further includes injecting neural stem cells into the vertebrate being at or proximate to the location of the spinal cord condition.

In one or more instances, the method of these teachings for treating a spinal cord condition in a vertebrate being further includes implanting a biomaterial into the vertebrate being at or proximate to the location of the spinal cord condition.

In one or more instances, the biomaterial is in the form of fibers, a scaffold, a sheet, a mesh or a tissue. In one or more instances, the biomaterial includes synthetic components, naturally-occurring components or combinations thereof. In one or more instances, the synthetic components are polymers. In one or more instances, the naturally-occurring components include heparin sulfate, chondroitin sulfate, keratin sulfate, hyaluronic acid, collagen, elastin, fibronectin, laminin or combinations thereof.

In one or more instances, the biomaterial is degradable or absorbable. In one or more other instances, the biomaterial is permanent.

In one or more instances, the biomaterial further includes cells. The cells can be neural cells, stem cells, neural stem cells, genetically engineered cells or combinations thereof.

In one or more instances, the constant direct current causes the injected neural stem cells to at least one of migrate, differentiate or proliferate relative to the spinal cord condition location.

In one or more instances, the constant direct current between the electrodes causes the injected neural stem cells to differentially express at least one of BDNF, NGF or HSP70.

In one or more instances, the constant direct current is provided as at least one of constant, non-varying, pulsed, varying, continuous and intermittent.

In one or more instances, at least one electrode conducting the constant direct current is located at least one of on the skin surface, subcutaneously, epidurally and subdurally.

In one or more instances, the spinal cord condition is associated with at least one of post-traumatic compression or disruption by fractured or displaced vertebra, disk herniation, cervical spondylosis, arteriovenous malformation, hemorrhage, multiple sclerosis, neuromyelitis optica, tranverse myelitis, Sjogren-related myelopathy, systemic lupus erythematosus, syringomyelia, meningomyelocele, tethered cord syndrome, vitamin B12 deficiency, amyotrophic lateral sclerosis, hereditary spastic paraparesis, spinal muscular atrophy or tropical spastic paraparesis/HTLV-1-associated myelopathy.

In one or more instances, the direct current is held constant by varying voltage between the electrodes in response to physiological changes of the vertebrate being.

In one or more instances, the spinal cord injury is remote from the first electrode.

In one or more instances, the method of these teachings for treating a spinal cord condition in a vertebrate being further includes providing DC power source having first and second terminals, providing a control circuit in electrical communication with at least one of the electrodes and the direct current source. The control circuit is configured to maintain constant current flow between the electrodes in response to changes in voltage across the first and second terminals.

In one or more instances, in the method of these teachings the direction of the constant direct current is alternated.

In one or more instances, the method of these teachings for treating a spinal cord condition in a vertebrate being further includes a) providing a constant direct current source having a plurality of terminals, b) providing a first of the terminals for connecting a first electrode to the direct current source, c) providing a second terminal for connecting a second electrode to the direct current source.

In one or more instances, the method of these teachings further includes providing a circuit to control the direction of current flow between the first electrode and the second electrode.

In one or more instances, the method of these teachings further includes providing a control circuit in electrical communication with at least one of the electrodes and the direct current source with the control circuit maintaining constant current flow between the electrodes in response to changes in voltage across the first and second terminals.

In one or more instances, the direct current source is a battery further including a stimulation system in a housing including supporting the direct current source and the terminals in the housing.

In one or more instances, the housing is wearable and configured to secure the direct current source to the vertebrate being and to permit the being to be mobile while the system is in operation.

In one or more instances, the method of these teachings for treating a spinal cord condition in a vertebrate being further includes providing a surface of the housing for presenting the first electrode as an electrode surface of the housing for attachment directly to the vertebrate being in the area of the dorsal aspect.

In one or more embodiments the stimulation device of these teachings for treating a spinal cord condition in a vertebrate being by applying stimulation at the dorsal aspect of the spinal cord at a site of the condition to regulate biological activity includes a) a direct current voltage source having a plurality of terminals, b) a first of the terminals for connecting a first electrode to the direct current source, c) a second of the terminals for connecting a second electrode to the direct current source, and d) a control circuit for controlling voltage available at the first and second terminals for enabling control of current flow between the electrodes.

In one or more instances, the control circuit further includes a signal controller circuit configured to maintain the current flow at a constant level between the first and second electrodes in response to changes in voltage across the first and second terminals.

In one or more instances, the stimulation device further includes an intelligent controller for executing stored routines for operation of the device.

In one or more instances, the stimulation device further includes a memory unit for providing data to the intelligent controller for operation of the device.

In one or more instances, the stimulation device further includes a signal controller circuit configured to be in electrical communication with at least one of the electrodes and the direct current source. The signal controller circuit being capable of controlling the character of current flow between the electrodes in response to changes in voltage across the first and second terminals for maintaining constant current flow between the electrodes.

In one or more instances, the direct current source is a battery and the terminals are associated with the battery.

In one or more instances, the stimulation device is configured to deliver trans-spinal direct current stimulation across a target section of the spine.

In one or more instances, the stimulation device includes an intelligent controller for executing stored routines for operating the device.

In one or more instances, the control circuit includes an on/off switch.

In one or more instances, the control circuit is configured to provide current flow including at least one of continuous, pulsed, intermittent, varying and non-varying current flow.

In one or more instances, the direct current source is a battery. The direct current source and the terminals are supported by a housing.

In one or more instances, the housing is wearable and configured to secure the direct current source to the vertebrate being and to permit the being to be mobile while the device is in operation.

In one or more instances, a surface of the housing includes an electrode surface for attachment of the first electrode directly to the being in the area of the dorsal aspect.

In one or more instances, the stimulation device of these teachings is a wearable package. The surface of the package is configured to be applied to a target dorsal location as an electrode. The surface is configured to present a conductive electrode connected to the DC source.

In one or more instances the surface includes an electrically conductive adhesive. In one or more alternate instances, the surface is magnetic and electrically conductive.

In one or more instances the wearable material includes an attachment device that includes at least one of a strap, cloth, elastic, harness or belt attachment configured to allow the electrode surface to be in contact with the skin of the vertebrate.

In one or more instances, the stimulation device includes at least one lead for the return electrode which is affixed to and runs along the attachment device to make electrical contact via the return electrode to provide the desired ventral electrical connection to the patient.

In one or more instances, the lead for the return electrode lead is connected to the current source with the connection being done by using at least one of a sealed pass-through or a port in the housing.

In one or more instances, the stimulation device is wearable and configured to be attached to the skin surface of the spine at one or more of the cervical, thoracic, lumbar or sacral levels depending on the site to be treated.

In one or more instances, the stimulation device includes an intelligent controller controlled by at least one of a human interface or internal circuit control using protocol data stored in a memory. The intelligent controller establishes a circuit connection between the electrodes and the terminals, respectively, according to data obtained from the memory to enable a treatment by a chosen protocol.

In one or more instances, a surface of the housing includes an electrode surface for attachment of the first electrode directly to the being in the area of the dorsal aspect.

In one or more embodiments the stimulation device of these teachings for treating a spinal cord condition in a vertebrate being by applying stimulation at the dorsal aspect of the spinal cord at a site of the condition to regulate biological activity of a least one of protein expression level or cell behavior to promote at least one of proliferation, differentiation, migration or expression includes a) a direct current source having a plurality of terminals, b) a first of the terminals for connecting a first electrode to the direct current source, c) a second of the terminals for connecting a second electrode to the direct current source, d) a circuit to control the direction of current flow between the first electrode and the second electrode, and e) a circuit in electrical communication with at least one of the electrodes and the direct current source. The circuit maintains constant current flow between the electrodes in response to changes in voltage at the first and second terminals and the direct current source is a battery.

In one or more instances, the stimulation device further includes a wearable housing configured to secure the direct current source to the vertebrate being and to permit the being to be mobile while the device is in operation.

In one or more instances, a surface of the housing includes an electrode surface for attachment of the first electrode directly to the being in the area of the dorsal aspect.

In one or more instances, the stimulation device further includes an intelligent controller for executing stored routines for delivering trans-spinal direct current stimulation during operation of the device.

In one or more instances, the stimulation device further includes a memory unit for providing data to the intelligent controller for operation of the device according to stored data.

In one or more instances, the intelligent controller controls the signal applied to the electrodes and controls the direction of current flow between the first electrode and the second electrode.

In one or more instances, the stimulation device further includes a signal controller circuit configured to be in electrical communication with at least one of the electrodes and the direct current source. The signal controller circuit being capable of controlling the character of the current flow between the electrodes in response to changes in voltage across the first and second terminals for maintaining constant current flow between the electrodes.

In one or more instances, the signal controller circuit is further configured to regulate the DC signal to provide the stimulation signal as at least one of constant, continuous, pulsed, intermittent, varying, or non-varying as directed by the intelligent controller.

In one or more instances, the direct current source is a battery and the terminals are associated with the battery.

In one or more instances, the stimulation device includes at least one of the electrodes including an array of electrodes. The array of electrodes is driven in a pattern according to a pattern controller circuit.

In one or more instances, the pattern controller circuit is instructed by the intelligent controller, which drives a desired stimulation pattern for the array of electrodes.

In one or more instances, the pattern controller circuit is configured to drive the array of electrodes to give target cells a rotational motion component or an angular motion component.

In one or more instances, the stimulation device includes a control circuit having a signal controller circuit for maintaining constant current flow, an intelligent controller circuit for control of the direction of current flow, a DC source, a user interface, and a memory, supported in a housing, having a configuration of at least one of benchtop, wearable, or implantable.

In one or more instances, the circuit for maintaining constant current flow between the electrodes includes a signal controller circuit configured to regulate the DC signal to provide the stimulation signal as at least one of constant, continuous, pulsed, intermittent, varying, or non-varying as directed by the intelligent controller circuit.

In one or more instances, the direct current source is a rechargeable battery.

In one or more instances, the housing is wearable and water tight.

BRIEF DESCRIPTION OF THE DRAWINGS

FIG. 1A-left is a photograph of an electrode system used in stimulating awake animals;

FIG. 1A-right is a photograph of an animal with the implanted electrodes connected to a DC stimulator;

FIGS. 1B-E are diagrams of experimental designs;

FIG. 3A: anodal stimulated animal: left panel is a photograph of a spinal transverse section, right panel is a graphic representation of the same section;

FIG. 3B: anodal stimulated animal: left panel is a photograph of a spinal transverse section, right panel is a graphic representation of the same section;

FIG. 3C: cathodal stimulated animal: left panel is a photograph of a spinal transverse section, right panel is a graphic representation of the same section;

FIGS. 7A-D are images from a confocal z-series of a section of spinal cord from an anodal stimulated animal in the area around the central canal;

FIGS. 7E-H are images from a confocal z-series of the same section of spinal cord from an anodal stimulated animal in a different location;

FIGS. 7I-L are images from a confocal z-series of the same section of spinal cord from an anodal stimulated animal in yet a different location;

FIG. 11 is a photograph of a Western blot and a graph of the relative amount of HSP70 protein in spinal cord after anodal tsDCS with respect to the control amount of $\beta$-actin;

FIG. 12A shows an embodiment of a wearable tsDCS device affixed on a patient;

FIGS. 12B-C show in plan and side view, respectively, an embodiment of the wearable device of FIG. 12A;

FIGS. 13A-L show the effects of repeated applications of tsDCS on cell number and cell migration;

FIGS. 14A-L show the immediate effects (i.e., after a short stimulation period) of tsDCS on cell migration;

FIGS. 15A-D show the effects of tsDCS on total cell number;

FIGS. 17A-G are images of sections: A-D stained with BrdU, row E double stained with BrdU and DCX, row F double stained with BrdU and GFAP, row G double stained with BrdU and NeuN.

DETAILED DESCRIPTION OF THE INVENTION

Figure 2A:
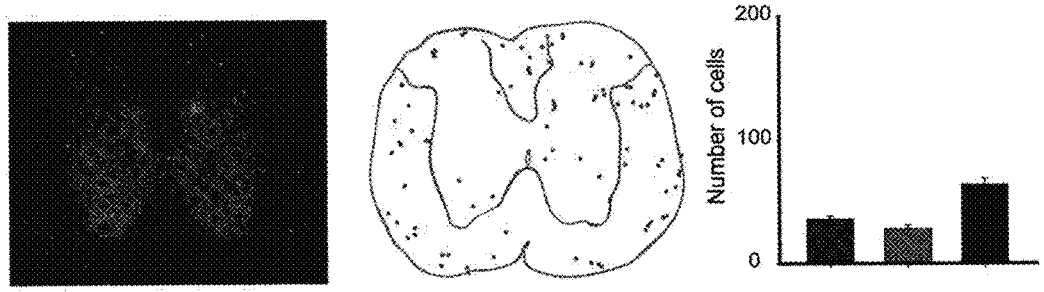
FIG. 2A: control animal: left panel is a photograph of a spinal transverse section, middle panel is a graphic representation of the same section, and right panel is a graph of the number of BrdU labeled cells in the section.

Trans-spinal direct current stimulation (tsDCS) is a non-invasive methodology that uses direct current to modulate spinal cord neurons. tsDCS can induce migration, proliferation and differentiation of specific cells within the spinal cord, and can induce or suppress expression of specific proteins within the spinal cord cells. The migration, proliferation and differentiation of specific cells can help rebuild spinal cord pathways that have been damaged or disrupted. The expression of specific proteins can suppress inflammatory processes and promote the formation of new neurons and connections.

According to the invention, tsDCS includes stimulation of a target spinal location between two electrodes. The stimulation includes direct current. The stimulation in one illustrative embodiment is substantially continuous and non-varying at subthreshold level. In another illustrative embodiment the stimulation is varying in whole or in part. In another illustrative embodiment the stimulation includes a combination of varying and non-varying stimulation. In another illustrative embodiment the stimulation includes pulses of stimulation. In yet another illustrative embodiment the stimulation includes pulses of continuous current stimulation where the current flow is not monodirectional. In practice of the invention, an electrode or array of electrodes is connected to a direct current source and placed at an area of interest on a proximal aspect of the body, such as either directly over or near the dorsal aspect of the spinal cord. A return electrode or array of electrodes is placed distal therefrom to define a current flow path which in practice can be on the ventral aspect of the body, but not necessarily, directly opposite the dorsal electrode. The direct current is applied to the proximally-placed dorsal electrode as either anode or cathode, depending upon function and desired stimulation.

In one or more embodiments, the present invention is directed to methods, devices and systems for treating a spinal disorder by applying a source of direct current to a spinal cord in animals, including humans and other sentient beings.

The following terms may be understood, in the various illustrative by not limiting descriptions of embodiments of invention provided herein, to at least have the following definitions:

"Cathodal stimulation" refers to tsDCS where the cathode is placed at the desired area of interest.

"Anodal stimulation" refers to tsDCS where the anode is placed at the desired area of interest.

"Proliferating cells" refers to cells that are actively dividing as a result of DCS. Actively dividing cells can be fluorescently labeled with BrdU. "Proliferate", "proliferating" and "proliferation" refer to an increase in the number of cells as a result of cell growth and cell division.

"Cell differentiation", "differentiation", "differentiate" and "differentiating" refers to the normal process whereby a cell changes from one cell type to another. Most commonly, this is a less specialized cell developing or maturing to possess a more distinct form and function.

"Migrate", "migrating", "migration", and "cell migration" refer to the movement of cells from one location to another. Tissue formation during embryonic development, wound healing and immune responses all require the orchestrated movement of cells in particular directions to specific locations. Cells often migrate in response to specific external signals, such as chemical signals, mechanical signals or direct current stimulation.

"Endogenous cells" refers to cells that originate from within an organism.

"Exogenous cells" refers to any cell that is present and active within an organism, but originated outside of that organism, and therefore must be introduced into the organism, e.g. by injection. Exogenous cells include stem cells and genetically engineered cells. Exogenous cells also include autologous cells, i.e. cells which are removed, stored and later given back to the same person, and allogenic cells which are from a donor that is different from the recipient.

"Neural cells" refers to cells of the nervous system including neurons and glial cells. Glial cells include astrocytes, oligodendrocytes, ependymal cells and microglia.

"Stem cells" are cells with the ability to divide and create an identical copy of themselves, and also with the ability to develop into mature tissue types. Embryonic stem cells are pluripotent cells with the ability to go on to form all the cells of the adult body. iPS cells, induced pluripotent stem cells are adult stem cells that have been genetically engineered to behave like embryonic stem cells. Adult stem cells are tissue-specific stem cells, which are committed to becoming one of the various cell types from their tissue of origin. For example, stem cells in the brain can form all the neurons and support cells of the brain, but cannot form non-brain tissues. "Neural stem cells (NSCs)" are self-renewing, multipotent cells that generate the main phenotype of the nervous system. Stem cells are characterized by their capability to differentiate into multiple cell types via exogenous stimuli from their environment. NSCs primarily differentiate into neurons, astrocytes and oligodendrocytes.

"Genetically engineered cells" refers to cells that have had their genome manipulated through biotechnology. In such cells, endogenous genes can be turned on or off, i.e. endogenous gene expression can be increased or decreased. Such cells also include those expressing exogenous genes that have been introduced into the cell.

"Expression" and "protein expression" refer to the level or amount of a protein or peptide contained within or produced by (e.g. excreted proteins or peptides) cells or tissues. "Differential expression", differential protein expression" and "differentially expressed" refer to a change in the level or amount of a protein or peptide contained within or produced by cells or tissues. Changes in protein or peptide expression as a result of cell differentiation. Changes in protein expression can occur in response to specific external signals, such as chemical signals, mechanical signals or direct current stimulation. Such changes in expression can be an increase or a decrease in the level or amount of protein or peptide contained within or produced by cells or tissues. An increase in the level or amount of protein or peptide is also referred to as "up-regulation", and a decrease in the level or amount of protein or peptide is also referred to as "down-regulation".

"Biomaterial" and "biocompatible material" refer to structures that can interact with or surround the spinal cord in an area of a site of a condition such as a spinal injury. The biomaterial or biocompatible material can be an exogenous material that is implantable and can be degraded or absorbed over time. Alternatively, the biomaterial or biocompatible material can be permanent. The biomaterial or biocompatible material can be in the form of fibers, a scaffold, a sheet, a mesh or a tissue, and can consist of synthetic or naturally-occurring components. Such synthetic components include polymers. Such naturally-occurring components include those of extracellular matrix (ECM), e.g., fibrous proteins, proteins and glycosaminoglycans (GAGs). GAGs are carbohydrate polymers, which are attached to proteins to form proteoglycans. Proteoglycans include heparin sulfate, chondroitin sulfate and keratin sulfate. Hyaluronic acid is a non-proteoglycan polysaccharide component of ECM. Fibrous proteins include collagen and elastin. Non-fibrous protein components of ECM include fibronectin and laminin. The biomaterial or biocompatible material can include: one or more of synthetic polymers, heparin sulfate, chondroitin sulfate, keratin sulfate, hyaluronic acid, collagen, elastin, fibronectin, laminin or combinations thereof. The biomaterial or biocompatible material can also include cells attached thereto or otherwise associated therewith. Such cells can include stem cells, neuronal stem cells or genetically engineered cells.

"HSP" refers to "heat shock proteins", are a family of proteins that are produced by cells in response to exposure to stressful conditions. Heat shock proteins are named according to their molecular weight, e.g. HSP60, HSP70, HSP80, HSP90. HSP70 has anti-apoptotic activity, i.e. it is involved in protecting cells from death.

"BDNF" refers to "brain-derived neurotrophic factor", a protein found in the brain and the periphery which acts on certain neurons of the central nervous system and the peripheral nervous system, helping to support the survival of existing neurons, and encourage the growth and differentiation of new neurons and synapses.

"NGF" refers to "nerve growth factor", a neuropeptide primarily involved in the regulation of growth, maintenance, proliferation, and survival of certain target neurons.

Illustrative embodiments of the invention includes treating spinal cord disorders or trauma using cathodal stimulation at the dorsal aspect of the spinal cord to increase the number of endogenous proliferating cells at the target site of injury (at or near the dorsal aspect). A return electrode (anode) is placed at a ventral location across the target site. A stimulating cathode electrode is applied to the dorsal aspect of the spinal column and a specified amount of current is applied for a specified period of time. Stimulation can be repeated at various intervals and for varying time periods to achieve a therapeutic effect.

Illustrative embodiments of the invention include treating spinal cord disorders or trauma using anodal stimulation at the dorsal aspect of the spinal cord to increase the number of endogenous proliferating cells at the site of injury (closer to the ventral aspect or throughout the spinal cord) to affect repair or recovery. A return electrode (cathode) is placed at a ventral location at or about an area distal to the anode across the target site. A stimulating anode electrode is applied to the dorsal aspect of the spinal column and a specified amount of current is applied for a specified period of time. Stimulation can be repeated at various intervals and for varying time periods to achieve a therapeutic effect.

Illustrative embodiments of the invention include treating spinal cord disorders or trauma using cathodal stimulation at the dorsal aspect of the spinal cord to increase the number of exogenous cells at the site of injury (at or near the dorsal aspect)) to affect repair or recovery. A return electrode (anode) is placed at a ventral location at or about an area distal to the anode across the target site. For example, neural stem cells are injected into a subject at or near an area of injury, and a stimulating cathode electrode is applied to the dorsal aspect of the spinal column and a specified amount of current is applied between the electrodes for a specified period of time in order to attract the stem cells to the dorsal aspect to affect repair or recovery. Stimulation can be repeated at various intervals and for varying time periods to achieve a therapeutic effect.

Illustrative embodiments of the invention include treating spinal cord disorders or trauma using anodal stimulation at the dorsal aspect of the spinal cord to increase the number of exogenous cells at the site of injury (closer to the ventral aspect or throughout the spinal cord) to affect repair or recovery. A return electrode (cathode) is placed at a ventral location at or about an area distal to the cathode across the target site. For example, neural stem cells are injected into a subject at or near an area of injury, and a stimulating anode electrode is applied to the dorsal aspect of the spinal column and a specified amount of current is applied for a specified period of time in order to direct the stem cells toward the ventral aspect or throughout the spinal cord to affect repair or recovery. Stimulation can be repeated at various intervals and for varying time periods to achieve a therapeutic effect.

Illustrative embodiments of the invention include treating spinal cord disorders or trauma using anodal stimulation at the dorsal aspect of the spinal cord to promote differentiation of endogenous neuronal cells at the site of injury (closer to the ventral aspect or throughout the spinal cord) to affect repair or recovery. A stimulating anode electrode is applied to the dorsal aspect of the spinal column and a specified amount of current is applied for a specified period of time. A return electrode (cathode) is placed at a ventral location at or about an area distal to the cathode across the target site. Stimulation can be repeated at various intervals and for varying time periods to achieve a therapeutic effect.

Illustrative embodiments of the invention include treating spinal cord disorders or trauma using anodal stimulation at the dorsal aspect of the spinal cord to promote differentiation of exogenous neuronal cells at the site of injury (closer to the ventral aspect or throughout the spinal cord) to affect repair or recovery. A return electrode (cathode) is placed at a ventral location at or about an area distal to the cathode across the target site. In one embodiment, neural stem cells are injected into a subject at or near an area of injury, and a stimulating anode electrode is applied to the dorsal aspect of the spinal column and a specified amount of current is applied for a specified period of time in order to direct the stem cells toward the ventral aspect or throughout the spinal cord to affect repair or recovery. Stimulation can be repeated at various intervals and for varying time periods to achieve a therapeutic effect.

Illustrative embodiments of the invention include treating spinal cord disorders or trauma using alternating cathodal and anodal stimulation at the dorsal aspect of the spinal cord to increase the number of endogenous proliferating cells at the site of injury (at or near the dorsal aspect) and to promote differentiation of endogenous neuronal cells to affect repair or recovery. The amount of time each current is applied to each electrode at the dorsal aspect can be varied to ensure that differentiating neurons remain at the site of injury. Stimulation can be repeated at various intervals and in varying alternating timing scenarios to achieve a therapeutic effect.

Illustrative embodiments of the invention include treating spinal cord disorders or trauma using alternating cathodal and anodal stimulation at the dorsal aspect of the spinal cord to increase the number of exogenous proliferating cells, such as neural stem cells introduced into a patient at or near the site of injury (at or near the dorsal aspect) and to promote differentiation of exogenous neuronal cells to affect repair or recovery. The amount of time each current is applied to each electrode at the dorsal aspect can be varied to ensure that differentiating neurons remain at the site of injury. Stimulation can be repeated at various intervals and in varying alternating timing scenarios to achieve a therapeutic effect.

Illustrative embodiments of the invention include treating brain trauma, stroke, Bell's palsy, cerebral palsy, Guillain-Barre syndrome, Parkinson's disease, multiple sclerosis, amyotrophic lateral sclerosis (ALS), Huntington's chorea or Alzheimer's disease. Illustrative embodiments of the invention include direct current treatments as described herein and in yet other combinations. For example, when exogenous cells are introduced into a subject and subsequently stimulated with direct current it is to be understood that endogenous cells at that position are also simultaneously stimulated.

Animals, particularly mammals including humans, are the subjects of the DCS treatments discussed herein. In illustrative and non-limiting embodiments, treatment of humans in practice of the invention can include application of tsDCS, for example, generally within a range of over 1 mA and under 6 mA, and more particularly within a range of about 3.5-4 mA, and can be applied for about 20-40 min/day. tsDCS treatment can be as often as indicated on a scheduled day or alternating days, or any other treatment regime intended to affect repair or recovery.

It will be appreciated now that the present invention enables manipulation and aggregation of biosubstances (e.g., endogenous cells, exogenous cells, proteins, DNA) of interest at locations of interest within a live subject (animal, human or other sentient being) as taught by the illustratively disclosed forms of direct current stimulation of the invention. This can be achieved in practice of embodiments of the present invention, for example, utilizing the illustrative stimulation devices and systems of FIGS. 10 and 12.

Figure 10A:
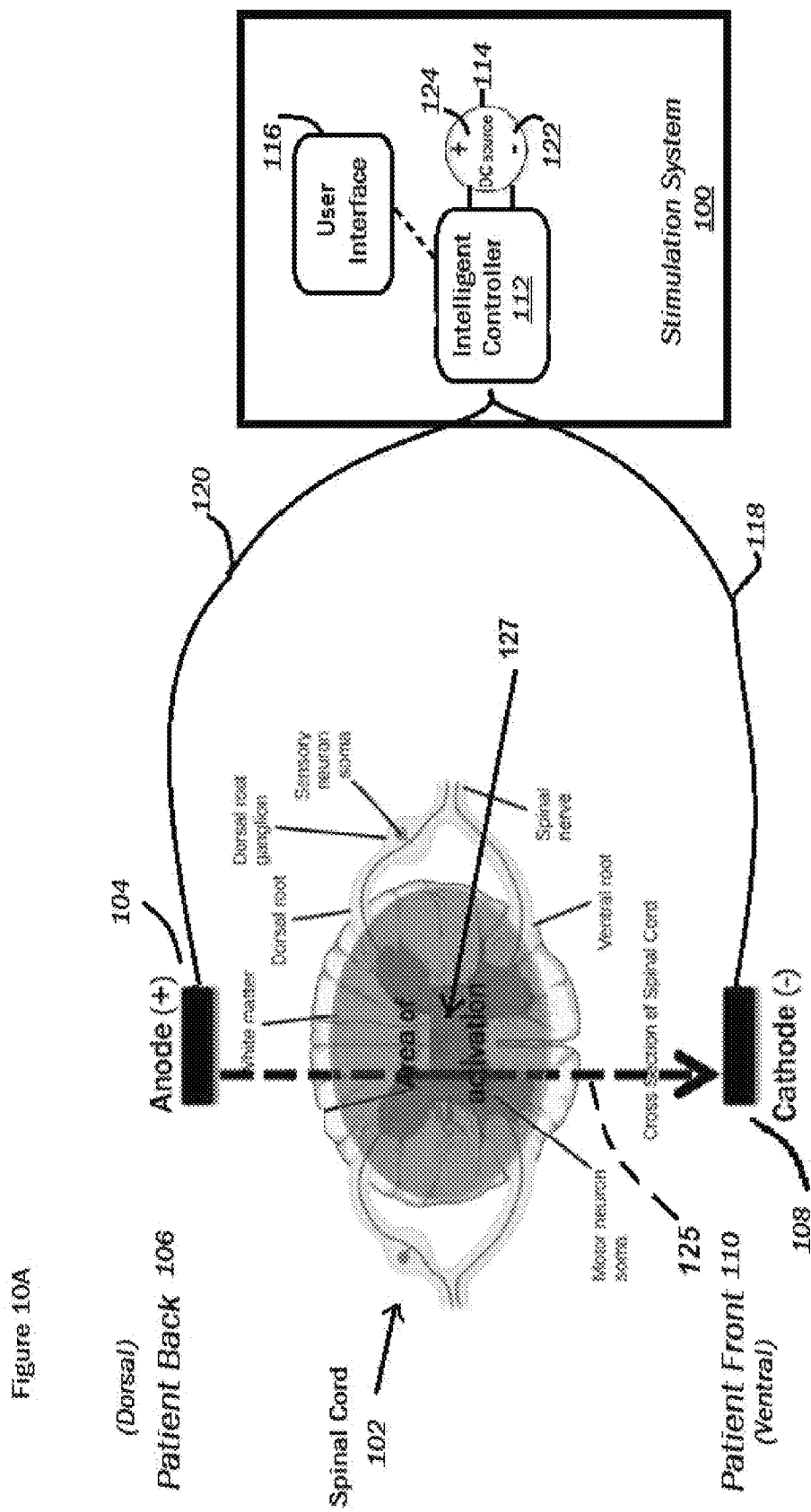
FIG. 10A shows an embodiment of a stimulation system of the invention configured to apply trans-spinal Direct Current Stimulation (tsDCS) stimulation to the spinal cord (dorsal to ventral)

FIG. 10A shows an embodiment of a stimulation of the invention configured to apply tsDCS stimulation to the spinal cord 102 (shown in cross-section) through application of electrode 104 on the dorsal side 106 at the spinal aspect 105 of the subject and location of an electrode 108 at an opposing ventral aspect 110, or other distal location, such as at the abdomen. Electrodes 104 and 108 are shown provided as anode and cathode, respectively, as an illustration only. In other embodiments, electrodes 104 and 108 are provided as cathode and anode, respectively. In various applications of the invention, the polarity of the electrode applied at the principal location, such as at the dorsal aspect 105 at a location of interest, defines the circuit configuration as either "anodal" or "cathodal".

In an illustrative embodiment of the invention of FIG. 10A, system 100 includes a direct current source 114 having terminals 122, 124. A first electrode 104 is attached to a first of the terminals and to a dorsal aspect 105 of a vertebrate being. A second electrode 108 is attached to a second of the terminals and to a target ventral location 110 of the vertebrate. The stimulation proceeds between dorsal electrode 104 and ventral side electrode 108. The current will proceed from anode to cathode, as assigned. Intelligent controller 112 controls the signal applied to such attached electrodes and thus controls the direction of current flow and thus defines the flow path 125 between the first electrode 104 and the second electrode 108.

In one illustrative practice of the invention, an anodal tsDCS configuration is established at the spinal cord 102 of a subject, as shown in FIG. 10A, where electrode 104 is made anodal as it is connected to the positive current source 124 by controller 112, and the return electrode 108 is cathodal, as connected to the negative current source 122, by controller 112, under direction of user interface 116. The return electrode is preferably applied on the corresponding ventral aspect although it may be offset or more distal depending upon the intended current flow path 125, such as shown in FIG. 10A, as will locate the area of activation 127 of such stimulation.

As will be appreciate by a person skilled in the art, in one embodiment, the intelligent controller 112 includes an internal instruction set and may be further informed via data from memory 117 or by user intervention at interface 116. Intelligent controller 112 enables application of current from DC source 114 to electrodes 104, 108. In one illustrative embodiment, the negative current source 122 of DC source 114 is connected to electrode 108 (now functioning as the cathode) via lead 118 and the positive current source 124 of DC source 114 is connected to electrode 104 via lead 120 (now functioning as the anode). In one embodiment, DC source 114 includes battery 115. In practices of the invention, the battery may be understood to include at least one of a capacitive storage device, a rechargeable device, a lithium-ion battery, and other electrical sources.

In illustrative embodiments of the invention, system 100 further includes a signal controller circuit 111 in electrical communication with at least one of the electrodes and with the direct current source, for maintaining constant current tsDCS current flow between electrodes 104, 108 in response to changes in voltage detected across the first and second terminals 122, 124, as will be understood by a person skilled in the art. In embodiments of the invention, signal controller circuit 111 is further configured to regulate the DC signal to provide the stimulation signal 126 as at least one of constant, continuous, pulsed, intermittent, varying, and non-varying as directed by controller 112. In various embodiments of the invention, various of these variations can be implemented as part of or added to the desired non-varying constant tsDCS stimulation of the invention to achieve a desired stimulation performance, as will be appreciated by a person skilled in the art.

In illustrative embodiments of the invention, the system of the invention has a control circuit including a signal controller circuit 111, intelligent controller circuit 112, DC source 114, battery 115, user interface 116, and memory 117 are supported in a housing 130, which may be for benchtop use or for use as a wearable or implantable device, and may be watertight, all in practice of embodiments of the invention.

In the illustrative embodiments of FIGS. 12A-C, a wearable housing system 200 includes the system 100 in a wearable housing 131 having a wearable attachment system 132. The wearable attachment system 132 enables presentation of the housing 131 as a slim and wearable package 134. In one practice of the invention, the back surface 138 of package 134 itself is applied to the target dorsal location 105, and, in one embodiment, is provided with a conductive electrode 104 defined by surface 140 and is connected to the internal DC source 114. Surface 140 may further include an electrically conductive adhesive 141, all to provide the desired signal at electrode 104 when attached on the vertebrate patient.

As shown in FIGS. 12A-C, in one illustration, the attachment system 132 further includes wearable material 133 such as straps 142, 144 (with connecting Velcro, buckles, or the like) to further secure system 100 to the patient. The return electrode 108 is connected to DC source 114 via lead 118 which in this illustrative embodiment is connected to the current source via a sealed passthrough or port 145 of housing 131 and then affixed to and running along the skin-side of strap 142 to make electrical contact via electrode 108 to provide the desired ventral electrical connection to the patient. The electrode lead can be attached to or contained within the wearable material 133. In a further illustrative embodiment shown in FIG. 12B, user interface 116 includes user control pad 119 including operator control 119A and indicator lights 119B, for enabling switching of modes of operation and providing indication thereof.

Wearable material 133 can be a strap, cloth, elastic, harness or other wearable material configured to allow the electrode surface to be in contact with the skin of the vertebrate. Alternatively, the electrode surface can be attached or affixed to the skin surface via an adhesive mounting or by implanted magnets. In various embodiments of the invention, the wearable material can be provided in varying sizes and form factors depending on the size of the vertebrate (e.g., adult or child) and depending on the spinal location being treated. Alternatively, the wearable material can be adjustable to accommodate subjects of varying sizes and spinal location being treated. The wearable material enables positioning the electrode 104 surface on the skin in the area of the dorsal aspect of the subject. The wearable tsDCS device can be rechargeable and can be removed at night for charging and comfort of sleep. The wearable tsDCS device can be attached to the skin surface of the spine at the cervical, thoracic, lumbar or sacral levels depending on the site to be treated.

It will be appreciated by a person skilled in the art that intelligent controller 112 is controlled such as from human interface 116 or internally using data stored in memory 117 to establish circuit connection between electrodes 104, 108 and the terminals 122, 124 of source 114 according to a given treatment protocol to be implemented, whether anodal or cathodal. The memory 117 may include one or a series of data matrices which can be accessed to inform controller 112, as will be understood by a person skilled in the art. For example, the system 100 could be applied to the human and then turned on to perform a routine whose commands are stored in memory 117, such as pulsations or periods of treatment over time, and which are accessed from time to time by a routine initiated at controller 112, for providing a desired stimulation treatment. However, it will be understood that in a simple practice of the invention, the stimulation device can be set as an anodal or cathodal system without needing the intelligent control components of stimulation system 100.

Figure 10B:
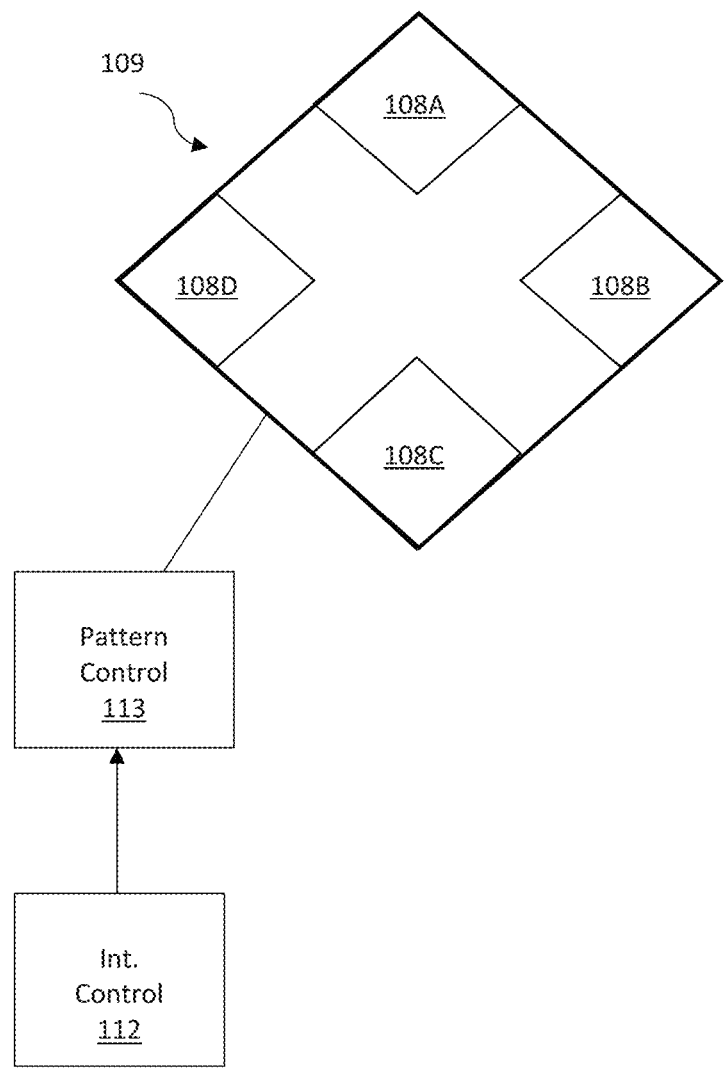
FIG. 10B shows an electrode array in practice of an embodiment of a stimulation system of the invention.

In a further illustrative embodiment, at least one of the cathode and anode electrodes is comprised of an array of component electrodes. In one illustrative practice thereof, the stimulation system 100 of FIG. 10A includes the electrodes 104 and 108 where, and as shown in the illustration of FIG. 10B, electrode 108 is comprised of an array 109 of electrodes 108A-D. In one illustrative practice of such an embodiment, each electrode of array 109 is capable of being separately stimulated whereupon the stimulated cells are favorably biased or steered toward achieving the desired stimulation goal.

In one illustrative embodiment of the invention, a pattern controller 113 is provided, and as instructed by intelligent controller 112, drives a desired stimulation pattern for the array of electrodes 108A-D. For example in one practice of this embodiment, the electrodes 108A-D of array 109 are sequentially stimulated so as to give target cells a rotational component. In another practice of this embodiment, or one or two of the electrodes is stimulated so as to give the target cells an angular component, as will enable direction of the movement of the target cells as needed to access its value at a target location. As a person skilled in the art will understand, this steering is analogous to the use of virtual steering done with DSP beam steering, such as used in the audio field, although here the purpose is steering various cells within the patient. In one embodiment, pattern controller 113 is incorporated into the wearable device 134 as shown in FIG. 12B.

It will now be appreciated that in practices of the invention, anodal tsDCS refers to stimulation with the anode associated with the dorsal aspect of the spinal cord and the cathode associated with the ventral aspect. Cathodal tsDCS refers to stimulation with the cathode associated with the dorsal aspect of the spinal cord and the anode associated with the ventral aspect.

In one illustrative practice of the invention, the presence of HSP70 protein at a desired spinal cord area of activation 127 is favorably increased associated with the location of the anode electrode 104, after a single session of anodal tsDCS stimulation of the circuit of FIG. 10A. In one illustrative embodiment, the stimulation session duration spans from 20 to 40 minutes to achieve this positive result. Multiple sessions are indicated for added positive results according to patient need. This increase in protein in the cells at the location under tsDCS anodal stimulation is demonstrated by increase of HSP70 as shown in FIG. 11.

Figure 9:
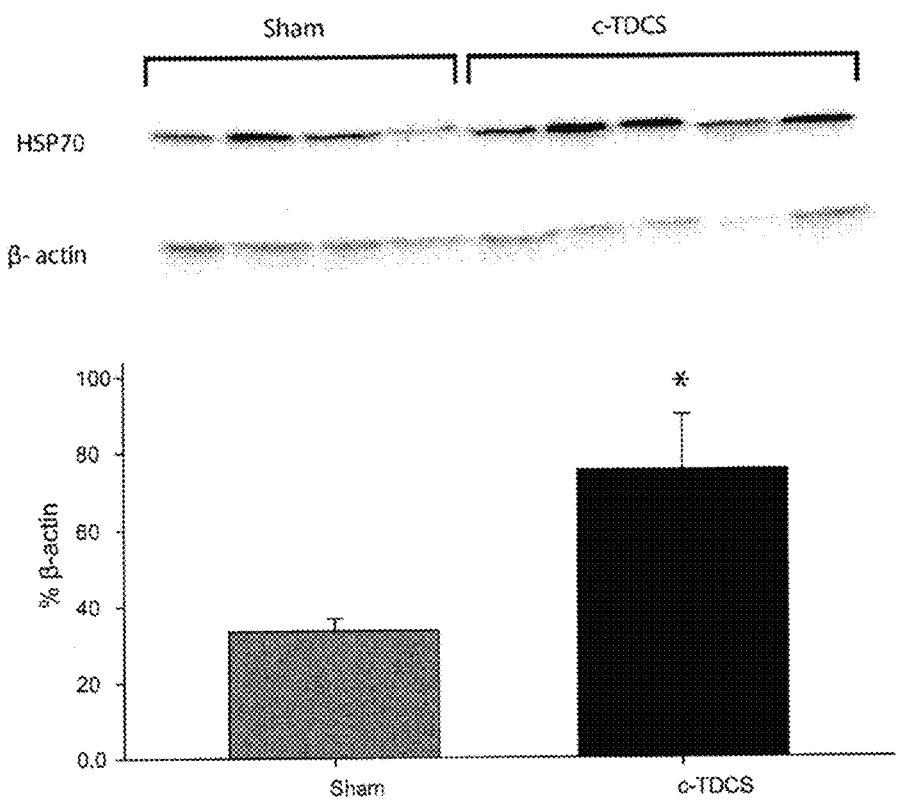
FIG. 9 is a photograph of a Western blot and a graph of the relative amount of HSP70 protein after cathodal DCS of the spinal cord with respect to the control amount of $\beta$-actin.

In another illustrative practice of the invention, in a cathodal tsDCS configuration using the system of FIG. 10A, electrode 104 is connected to negative source 122 and is applied at a desired dorsal location 105 and the anodal electrode is applied ventrally and is connected to the positive source 124, by controller 112. An increase of protein in the cells at the desired spinal cord area of activation 127 under cathodal tsDCS stimulation is demonstrated by increase of HSP70 as shown in FIG. 9. In one illustrative embodiment, the stimulation session duration spans from 20 to 40 minutes to achieve this positive result. Multiple sessions are indicated for added positive results according to patient need.

It will be appreciated by a person skilled in the art that the return electrode 108 is preferably applied on the corresponding ventral aspect although it may be offset or more distal depending upon the intended current flow path 125. In an illustrative practice of the invention, the return electrode 108 is applied opposite to the distal stimulation electrode 104 at the spine or at an aspect of the cranium, the neck, torso or an extremity, depending upon the intended current flow path 125 and intended area of activation 127. The present invention is further illustrated by the following specific example of tsDCS in a mouse model. The example is provided for illustration only and is not to be construed as limiting the scope or content of the invention in any way.

Example

Surgery and Electrode Implantation

Mice were deeply anesthetized with ketamine/xylazene (90/10 mg/kg, i.p.). Incisions were made at skin covering the dorso-lumbar spinal column, and the skin covering the cervical region. The tsDCS electrode was sutured fabric side down to the fascia of the spine to cover the area from the T13 to the L6 vertebral level. The reference electrode was placed fabric side up toward the lateral abdominal skin.

The spinal DCS electrodes consisted of a small stainless-steel plate (1.5 mm width; 3 mm length; 50 μm thick) that was sandwiched between silicone rubber (178 μm thick) and soft cotton-wick fabric (0.5 mm thick). The three layers were bonded together using silicone adhesive and left overnight to dry before use. The final DCS electrode was 10 mm wide and 15 mm long. Current strength used in all experiments was 0.8 mA. BrdU was injected at a dose of 250 mg/kg i.p.

Cathodal tsDCS refers to stimulation with the cathode located at the dorsal aspect of the spinal cord and the anode located at the ventral aspect. Anodal tsDCS refers to stimulation with the anode located at the dorsal aspect of the spinal cord and the cathode located at the ventral aspect.

Tissue Preparation

Animals were transcardinally perfused with PBS, 0.1 M at pH 7.4 for 4 min. followed with 4% paraformaldehyde (PFA/PBS). Tissues were post fixed for 24 hrs in 4% PFA then transferred into 30% sucrose for another 24 hrs. Spinal cords were cut into three parts: below the tsDCS electrode (i.e., caudal), under the electrode, and above the electrode (i.e., cranial). Every segment was placed in a separate vial. Thin transverse sections (30 μm) were cut using a cryostat. The brains were also collected to be used as positive control for DCX antibody binding and BdrU staining.

Cell Markers

Doublecortin (DCX) is a microtubule-associated protein expressed by neuronal precursor cells and immature neurons in embryonic and adult cortical structures. Neuronal precursor cells begin to express DCX while actively dividing, and their neuronal daughter cells continue to express DCX for 2-3 weeks as the cells mature into neurons. Downregulation of DCX begins after 2 weeks, and occurs at the same time that these cells begin to express, NeuN, a marker for mature neurons.

Due to the nearly exclusive expression of DCX in developing neurons, this protein has been used increasingly as a marker for neurogenesis. Indeed, the levels of DCX expression increase in response to exercise, which occurs in parallel with increased BrdU labeling, currently a "gold standard" in measuring neurogenesis.

Bromodeoxyuridine (5-bromo-2-deoxyuridine, BrdU) is a synthetic analog of the nucleoside thymidine. It is incorporated into replicating DNA in dividing cells.

Glial fibrillary acidic protein (GFAP) is a marker for glial cells. In particular, GFAP is an intermediate filament protein that is expressed by glial cells including astrocytes and ependymal cells.

NeuN (neuronal nuclei) is a marker expressed in mature neurons. NeuN immunoreactivity becomes obvious as neurons mature, typically after they have downregulated expression of DCX.

Nestin is an intermediate filament protein expressed in dividing cells during the early stages of development in the central nervous system (CNS), peripheral nervous system (PNS) and in myogenic and other tissues. Upon differentiation, nestin becomes downregulated and is replaced by tissue-specific intermediate filament proteins. Interestingly, nestin expression is reinduced in the adult during pathological situations, such as the formation of the glial scar after CNS injury and during regeneration of injured muscle tissue. In adult organisms nestin is expressed in neuronal precursor cells.

Pre-Treatment for Antibody

Floating sections were incubated in 50% formamide/2× SSC solution for 2 hours at 55° C. water bath then washed a single time with 2×SSC for 5 mins. Sections were treated with 1N HCl on ice for 10 min then with 2N HCl at 40° C. for 20 min sections then washed with 0.1 M boric acid (pH 8.5) for 10 min at room temperature (rmt) then washed 3× with 1×TBS, 10 min each at room temperature (rmt).

Sections were incubated in doublecortin (DCX) blocking solution for 1 hr at rmt, followed by incubation in goat-anti-DCX primary antibody (1:500) overnight at 4° C. sections were washed with 1×PBS three times for 10 minutes each at rmt followed by incubation in rabbit-anti-goat secondary antibody (2:750) for 2 hr at rmt. After washing with 1×PBS three times for 20 min each at rmt, sections were incubated in BrdU blocking solution (0.1% Triton X, 3% NGS, and 1×TBS) for 2 hr at rmt. Sections were then incubated in mouse-anti-BrdU primary antibody (1:100) for 48 hr at 4° C. next sections were washed and incubated in goat-anti-mouse fluorescently-labeled (488 nm) secondary antibody (1:500) for 2 hr at rmt. Sections were then washed and mounted using antifade with DAPI to stain cell nuclei as a second control. Slides were allowed to dry for 2 hr.

FIG. 1B is a diagram of Experiment 1 design. Three days after surgery to implant electrodes, animals were injected with BrdU for five days (250 mg/kg, ip; two 125 mg/kg injections, one in am and one in pm). tsDCS (40 min/day; was started one day after BrdU injection and ended one day after last BrdU injection. Animals were sacrificed immediately after the last stimulation session. Staining: BrdU; BrdU/DCX; BrdU/GFAP; BrdU/NeuN.

FIG. 1C is a diagram of Experiment 2 design. BrdU was injected for two days only followed by electrical stimulation for 60 min under anesthesia. Animals were then sacrificed and tissue processed for immunostaining. Staining: BrdU; BrdU/DCX; BrdU/GFAP; BrdU/NeuN.

FIG. 1D is a diagram of Experiment 3 design. Animals were injected with BrdU and trained to walk in a split wheel. This procedure lasted for 5 days, then animals were immediately sacrificed. Training was for 4 hours a day with period of rests. Staining: BrdU; BrdU/DCX; BrdU/GFAP; BrdU/NeuN.

FIG. 1E is a diagram of Experiment 4 design. Three days after surgery to implant electrodes, animals were injected with BrdU for five days (250 mg/kg, ip; two 125 mg/kg injections, one in am and one in pm). tsDCS (40 min/day) was started one day after BrdU injection and ended one day after last BrdU injection. Animals were sacrificed 30 days after the last stimulation session. Staining: BrdU; BrdU/NeuN; BrdU/DCX; BrdU/GFAP.

FIG. 2 shows the effects of tsDCS on BrdU labeled cells mobility and proliferation. Experiment 1 design: Animals were stimulated for 5 consecutive days (current intensity, 0.8 mA; duration, 40 min/day). Animals were also injected with BrdU for 5 consecutive days. Injections of BrdU were done starting one day prior to beginning stimulation.

Figure 4:
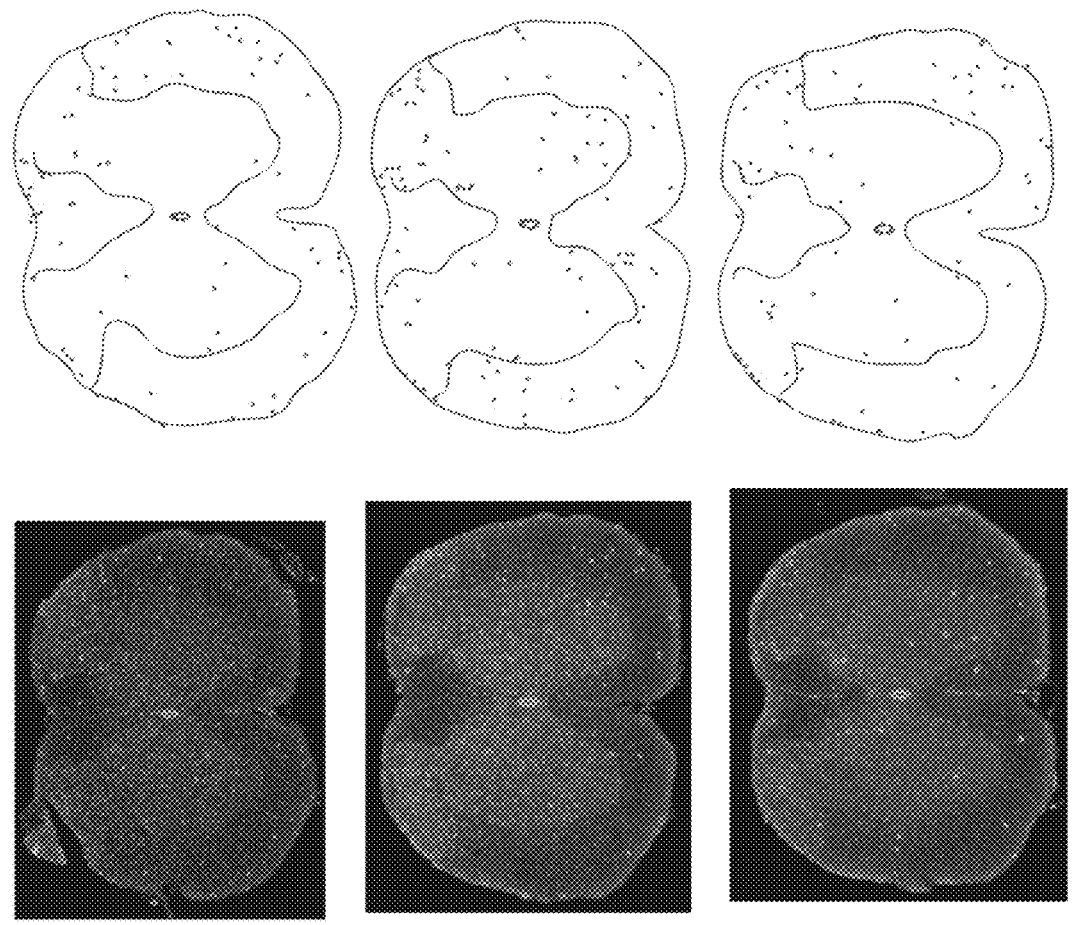
FIG. 4 is photographs of three spinal transverse sections from a control animal with corresponding graphic representations of the same sections.
Figure 8:
FIG. 8 is graphic representations of sections from five control animals, each row shows three representative sections from one animal.

FIG. 2A shows the results for the control animals (n=5): BrdU injection only for 5 consecutive days. The left panel shows a spinal transverse section; the middle panel is a graphic representation of the same section for clarity; and the right panel is a graph of the average number of cells that include BrdU labeled cells above (dorsal), and below (ventral) a horizontal line drawn at the spinal canal, and the total number of cells (total) labeled with BrdU. A total of about 65 dividing cells was observed with nearly equal distribution between the dorsal and ventral aspects and throughout the spinal cord (number of sections=14). FIGS. 4 and 8 are further spinal cord sections from control animals showing similar results.

Figure 2B:
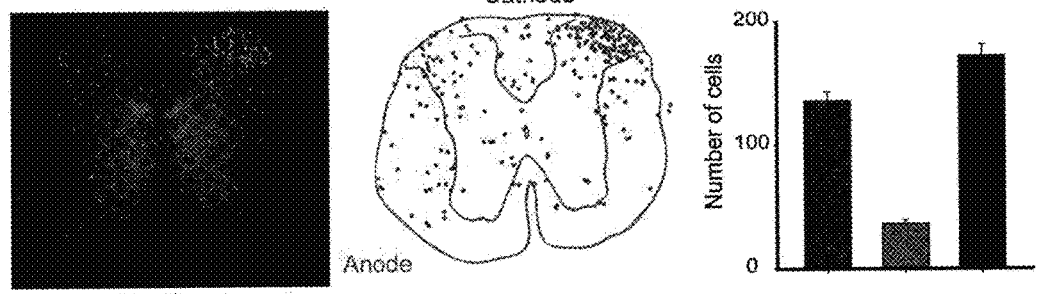
FIG. 2B: cathodal stimulated animal: left panel is a photograph of a spinal transverse section from the area under the electrode, middle panel is a graphic representation of the same section, and right panel is a graph of the number of BrdU labeled cells in the section.

FIG. 2B shows the results for cathodal stimulated animals (n=7). BrdU labeled cells accumulated toward to cathodal electrode situated over the dorsal aspect of the spinal column. This indicates either a migration of proliferating cells toward the cathode or an increase in proliferation of cells already resident in that area. The total number of dividing cells increased to about 170 with about 135 dividing cells (approximately 80%) concentrated in the dorsal aspect and about 35 dividing cells (approximately 20%) in the ventral aspect (number of sections=21).

Figure 5:
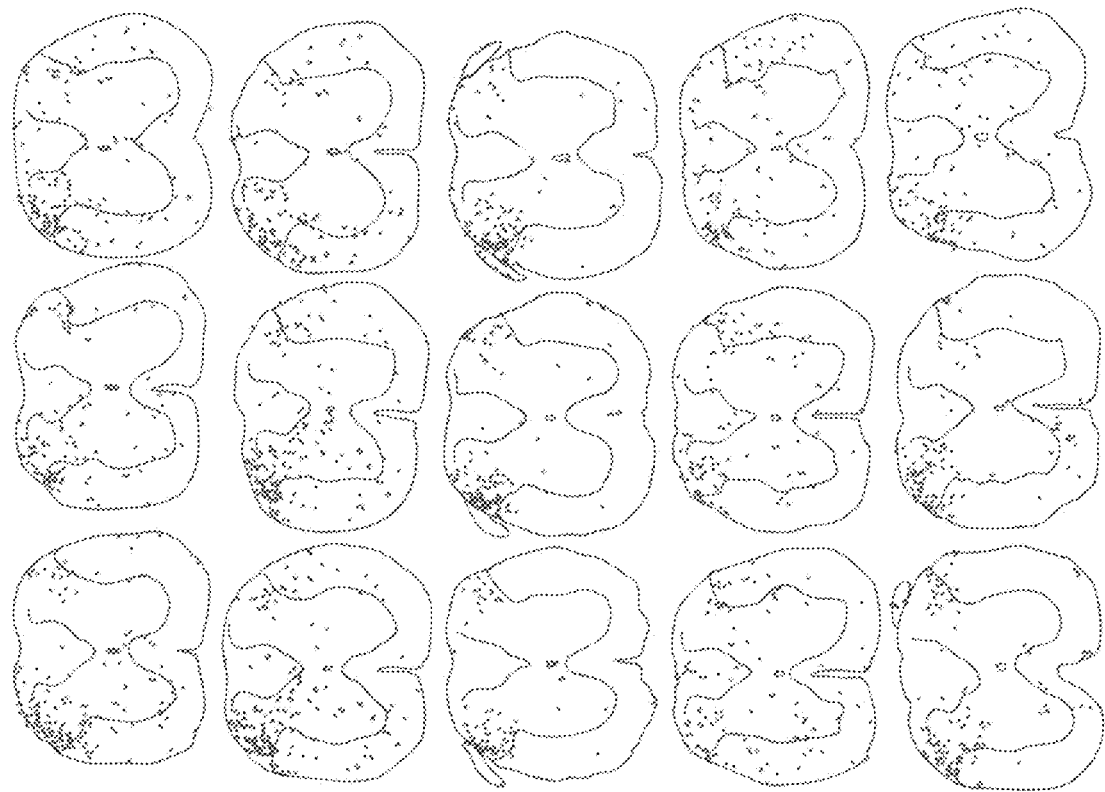
FIG. 5 is graphic representations of sections from five cathodal stimulated animals, each row shows three representative sections from one animal.

FIGS. 3 and 5 include further spinal cord sections from cathodal stimulated animals showing similar results.

Figure 2C:
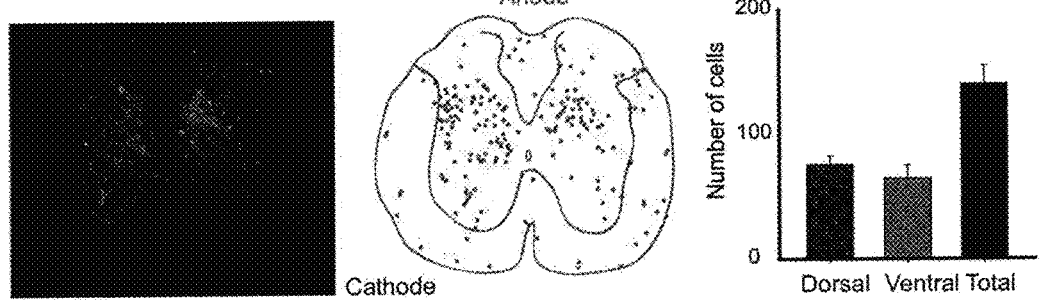
FIG. 2C: anodal stimulated animal: left panel is a photograph of a spinal transverse section from the area under the electrode, middle panel is a graphic representation of the same section, and right panel is a graph of the number of BrdU labeled cells in the section.
Figure 6:
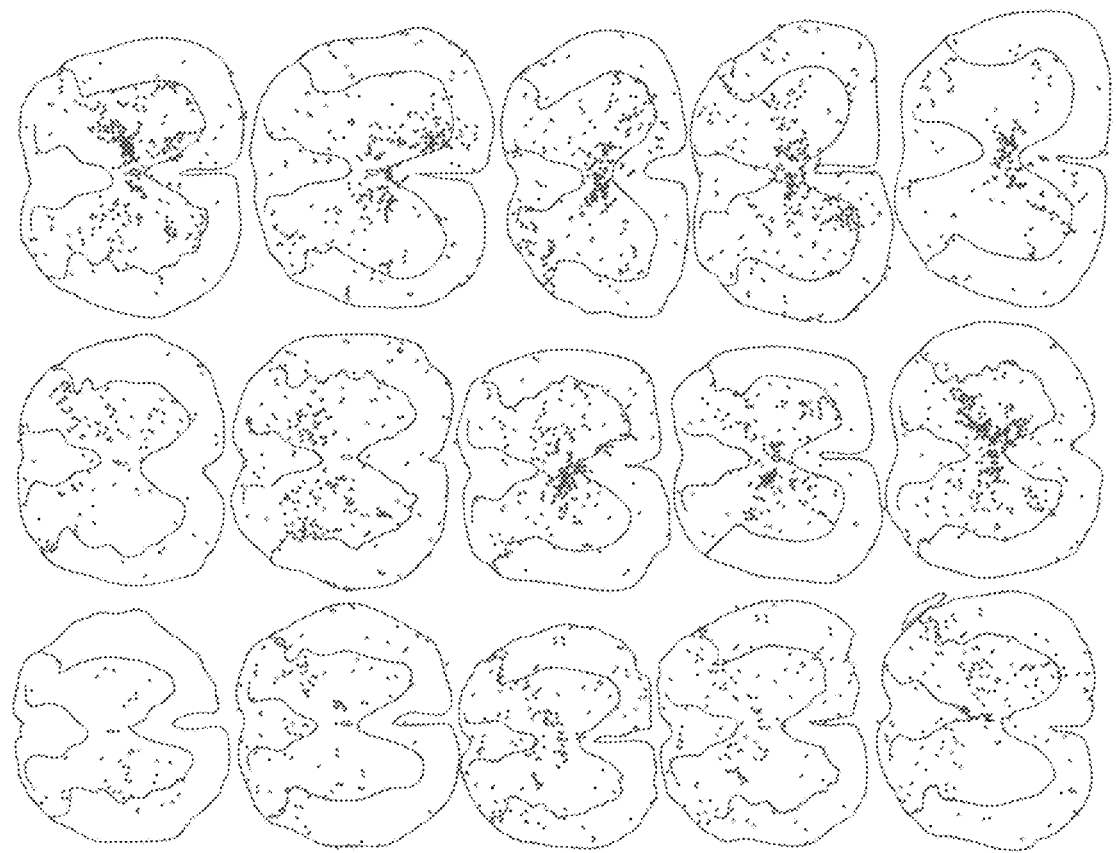
FIG. 6 is graphic representations of sections from one anodal stimulated animal.

FIG. 2C shows the results for anodal stimulated animals (n=5). Although there was a similar increase in the total number of BrdU labeled cells as seen with cathodal stimulation, the cells were fairly evenly distributed between the dorsal and ventral aspects. The total number of dividing cells increased to about 150 with nearly equal distribution between the dorsal and ventral aspects (number of sections=14). FIGS. 3 and 6 include further spinal cord sections from anodal stimulated animals showing similar results.

The results in FIG. 2 show that cathodal tsDCS causes an increase in the number of BrdU-labeled cells and causes an increase in the number of BrdU-labeled cells to accumulate at the dorsal aspect of the spinal cord. Anodal tsDCS also causes an increase in the number of BrdU-labeled cells, but there is a shift in the location of the BrdU-labeled cells toward the ventral aspect such that the distribution between the dorsal and ventral aspects is about even.

FIG. 13 shows further results for cathodal and anodal stimulated animals following treatment according to Experimental 1 design: animals were stimulated for 5 consecutive days (current intensity, 0.8 mA; duration, 40 min/day). Animals were also injected with BrdU for 5 consecutive days. Injections of BrdU were done starting one day prior to beginning stimulation. Panels A-D are a representative spinal transverse section from sham control, i.e. no current; panels F-H are a representative spinal transverse section from cathodal stimulated mice (cathode at the dorsal aspect); and panels I-L are a representative spinal transverse section from anodal stimulated mice (anode at the dorsal aspect). Panels A, F and I are a trace of the section indicating the locations of the BrdU-stained cells overlayed with a grid (the horizontal line between numbers 4 and 5 indicates the location of the central canal). Panels B, G and J are a heat map or contour map of the same sections. Panels C, E and K are a quantification of the average number of BrdU-stained cells in each of rows 1-8 from top to bottom (i.e., from the dorsal aspect to the ventral aspect). Panels D, H and L are bar graph representations of the percentage of BrdU-stained cells in the dorsal aspect versus the ventral aspect (i.e., a quantification of the number of cells above the central canal line (dorsal) as compared to the number of cells below the central canal line (ventral).

The results in FIG. 13 show that anodal and cathodal tsDCS increase the number of BrdU-labelled cells. The cathodal tsDCS stimulated group, showed a clear shift in the cell distribution toward the dorsal aspect of the spinal cord especially toward the dorsal horns, whereas the anodal tsDCS group, showed a clear shift of cell distribution toward the central aspect of the spinal cord, away from the electrode.

FIG. 14 shows results for cathodal and anodal stimulated animals following treatment according to Experimental 2 design: Animals were injected with BrdU for 5 consecutive days followed by one session of tsDCS under anesthesia (current intensity, 0.8 mA; duration, 60 min). Panels A-D are a representative spinal transverse section from sham control, i.e. no current; panels F-H are a representative spinal transverse section from cathodal stimulated mice (cathode at the dorsal aspect); and panels I-L are a representative spinal transverse section from anodal stimulated mice (anode at the dorsal aspect). Panels A, F and I are a trace of the section indicating the locations of the BrdU-stained cells overlayed with a grid (the horizontal line between numbers 4 and 5 indicates the location of the central canal). Panels B, G and J are a heat map or contour map of the same sections. Panels C, E and K are a quantification of the average number of BrdU-stained cells in each of rows 1-8 from top to bottom (i.e., from the dorsal aspect to the ventral aspect). Panels D, H and L are bar graph representations of the percentage of BrdU-stained cells in the dorsal aspect versus the ventral aspect (i.e., a quantification of the number of cells above the central canal line (dorsal) as compared to the number of cells below the central canal line (ventral).

The results in FIG. 14 show that cell distribution in slices from cathodal-stimulated tsDCS animals shifted toward the electrode located on the dorsal aspect of the spinal cord and from anodal-stimulated tsDCS animals shifted toward the ventral aspect of the spinal cord when compared to sham-control where there was no significant difference in distribution of cells above and below the horizontal central line.

FIG. 15 shows further results for cathodal and anodal stimulated animals following treatment according to Experimental 1 design as described above. The results in FIG. 15 show that cathodal, and anodal tsDCS increased the number of BrdU stained cells. A, representative spinal cord slice from sham-control animal. B, representative spinal cord slice from cathodal tsDCS stimulated animal. C, representative spinal cord slice form anodal tsDCS stimulated animal. D, summary graph showing the total number of cells (5 slices/animal).

FIGS. 7A-L show the co-localization of BrdU and DCX in spinal cord stimulated with anodal tsDCS. Figures A-D show a confocal z-series taken from an area around the central canal. Double stained cells are orange/yellow. Figures E-H show a z-series taken from a different location in the same section. There are both single and double stained cells. Figures I-L show a z-series taken from the same section. It shows BrdU-labeled cells (green; magenta arrows) extending a process through the white matter, and a group of BrdU/DCX double labeled (blue arrows) cells following the track made by the process.

Anodal tsDCS shows an increase in the number of BrdU/DCX double-labeled cells indicating a possible manipulation of cell fate.

FIGS. 17A-G show the results of co-staining of sections from anodal-stimulated animals according to Experimental 1 design as described above. Panels A-D are sections stained with BrdU only. Row E is a confocal z-series of a section stained with BrdU and DCX. Row F is a confocal z-series of a section stained with BrdU and GFAP. Row G is a confocal z-series of a section stained with BrdU and NeuN.

The results in FIG. 17 show that few elongated smaller cells were double stained with DCX (arrows), which were the newly divided neural progenitors from previous rounds of cell division. Cells double-stained with BrdU and GFAP (arrows) were also smaller in shape, newly formed differentiated cells which will eventually form glial cells. There were no cells stained with NeuN.

Figure 16:
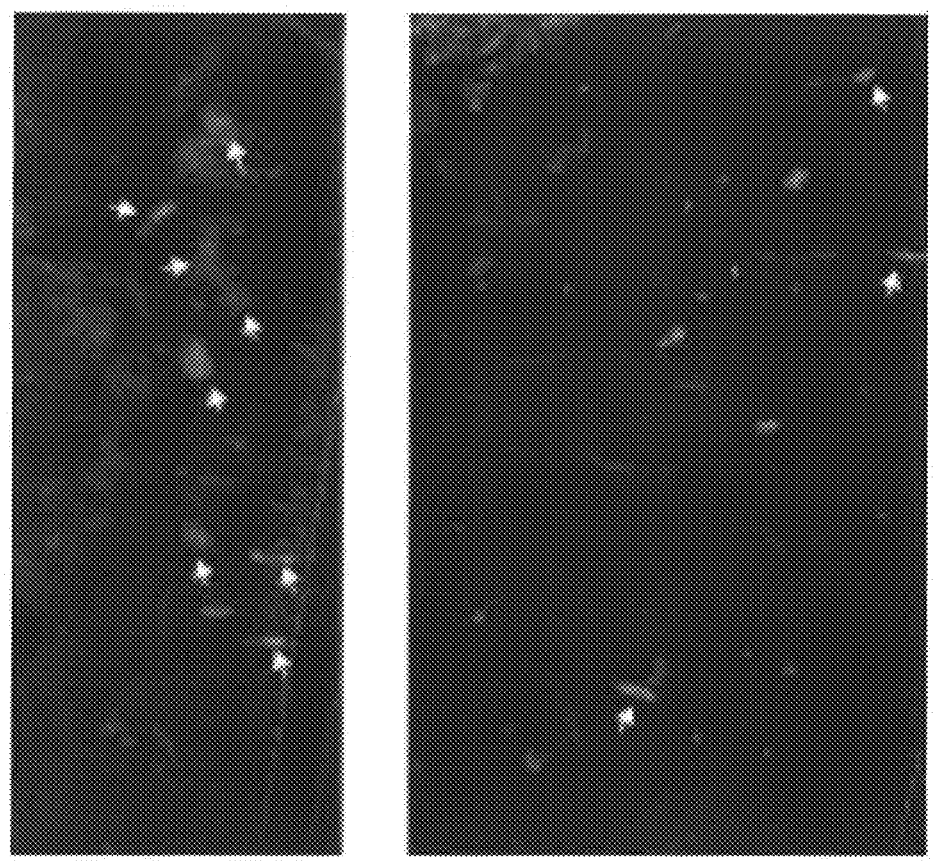
FIG. 16 is images of sections showing cells double stained with BrdU and nestin.

FIG. 16 shows the results of co-staining of sections from stimulated animals according to Experimental 2 design as described above. Cells double stained with BrdU (green) and Nestin (red), show neural stem cells which proliferated (arrows).

Mice were stimulated for 5 days for 20 min/day with the cathode on the motor cortex region of the brain and the reference electrode on the tail of the mice. 72 hours after the final stimulation the mice were sacrificed and motor cortex tissue was collected and homogenized with RIPA buffer (10 mM Tris pH 7.4, 100 mM NaCl, 1 mM EDTA, 20 mM $Na_4P_2O_7$, 20 mM $Na_3VO_4$, 0.5% deoxycholate, 1 mM PMSF) and a protease inhibitor cocktail from Roche and sonicated about 3-4 min to completely homogenate. Total protein concentration was determined using the Lowry assay and 20 micrograms of total protein was resolved in each lane by 10% sodium dodecyl sulfate polyacrylamide gel electrophoresis (SDS-PAGE) and transferred to a nitrocellulose membrane. The membrane was blocked in Tris-buffer saline containing 1% defatted milk and 0.05% Tween 20 (TTBS) and incubated overnight with the primary antibody at 1:1000 dilution in the blocking buffer at 4° C. The next day, after three washes with TTBS, the blots were incubated with the secondary antibody at 1:5000 dilution in the blocking buffer for 1 hr and the blots were imaged using chemiluminescence. The protein bands obtained were quantified using the software Image J. The results are shown in FIG. 9, and indicate about double the amount of HSP70 being expressed in motor cortex of the cathodal stimulated mice as compared to control mice.

Mice were stimulated for 5 days for 40 min/day with the anode on the dorsal aspect of the spinal cord and the reference electrode on the stomach of the mice. 72 hours after the final stimulation the mice were sacrificed and spinal cord tissue from under the applied anode was collected and homogenized with RIPA buffer (10 mM Tris pH 7.4, 100 mM NaCl, 1 mM EDTA, 20 mM $Na_4P_2O_7$, 20 mM $Na_3VO_4$, 0.5% deoxycholate, 1 mM PMSF) and a protease inhibitor cocktail from Roche and sonicated about 3-4 min to completely homogenate. Total protein concentration was determined using the Lowry assay and 20 micrograms of total protein was resolved in each lane by 10%/o sodium dodecyl sulfate polyacrylamide gel electrophoresis (SDS-PAGE) and transferred to a nitrocellulose membrane. The membrane was blocked in Tris-buffer saline containing 1% defatted milk and 0.05% Tween 20 (TTBS) and incubated overnight with the primary antibody at 1:1000 dilution in the blocking buffer at 4° C. The next day, after three washes with TTBS, the blots were incubated with the secondary antibody at 1:5000 dilution in the blocking buffer for 1 hr and the blots were imaged using chemiluminescence. The protein bands obtained were quantified using the software Image J. The results are shown in FIG. 11, and indicate almost double the amount of HSP70 being expressed in spinal cord of the anodal stimulated mice as compared to control mice.

Figure 18A:
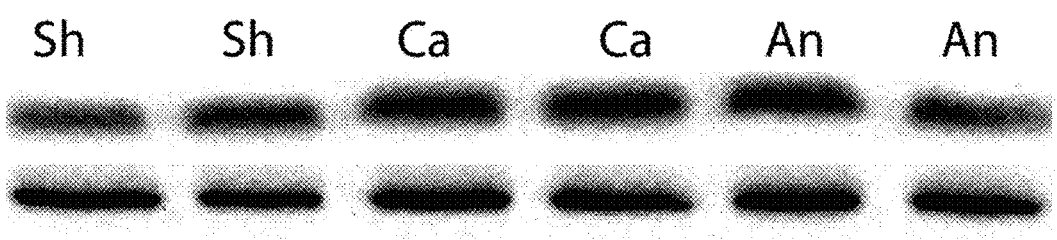
FIGS. 18A-B are photographs of Western blots of the relative amount of BDNF protein (A) and NGF protein (B) after 20 minutes of tsDCS with respect to the control amount of $\beta$-actin.
Figure 18B:
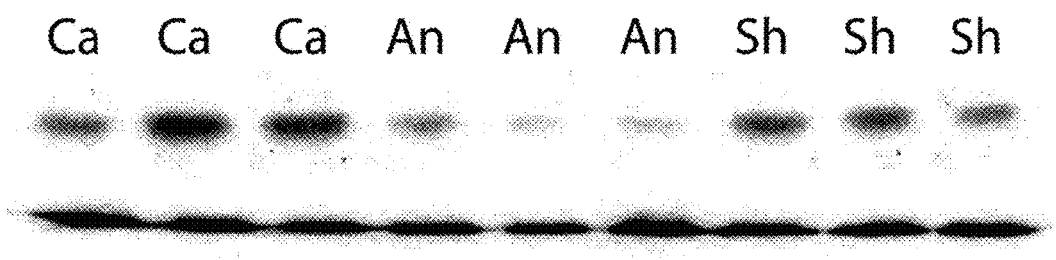

FIGS. 18A-B are Western blots of total protein isolated from isolated spinal cord tissue from animals subjected to 20 min/day of tsDCS for 5 days. The blots were incubated with antibodies directed to BDNF (A) and NGF (B); bottom row of each panel is β-actin control for the amount of protein. The Western blotting analysis of BDNF showed that both anodal and cathodal stimulation increased BDNF expression when compared with the control. The Western blotting analysis of NGF showed that cathodal stimulation increased NGF expression but anodal stimulation decreased NGF expression when compared with the control.

In summary, BrdU-labeled cells migrate towards the cathodal tsDCS electrode or toward the dorsal aspect of the spinal cord. BrdU-labeled cells migrate away from the anodal tsDCS electrode or toward the central aspect of the spinal cord. Both cathodal and anodal tsDCS increase the number of BrdU-labelled cells. The newly formed cells, larger in size, are usually still in the proliferative stage and not yet differentiated. Some of the longer-term effects of tsDCS may be mediated through the differential expression of HSP70 and/or growth factors, such as BDNF and NGF.

The foregoing description is illustrative experimental validation of the present invention. It will now be appreciated that tsDCS stimulation according to embodiments of the invention is practiced non-invasively using direct current stimulation to modulate spinal cord neurons. It will now be appreciated that tsDCS can induce migration, proliferation and differentiation of specific cells within the spinal cord, and can induce or suppress expression of specific proteins within the spinal cord cells. This activity helps rebuild spinal cord pathways that have been damaged or disrupted, while the expression of specific proteins suppresses inflammatory processes and promotes the formation of new neurons and connections, in practices of the invention.

While these teachings have been described in terms of specific embodiments, it is evident in view of the foregoing description that numerous alternatives, modifications and variations will be apparent to those skilled in the art. Accordingly, these teachings are intended to encompass all such alternatives, modifications and variations which fall within the scope and spirit of the present teachings and the following claims.

What is claimed is:

1. A method of treating a spinal cord condition in a vertebrate being, comprising the steps of:
applying stimulation between an anode and cathode of a direct current source with one of the anode and cathode stimulating a dorsal aspect of a spinal cord of a vertebrate being at a spinal location associated with a spinal cord condition of the being;
regulating biological activity of at least one of protein expression level and cell behavior in the spinal location;
applying the direct current stimulation at an intensity and for a period of time sufficient to cause the biological activity to include at least one of proliferation, differentiation, migration and expression in the spinal location;
wherein the direct current is a constant direct current applied between a first electrode and a second electrode, the first electrode being at or proximate to the dorsal aspect of the spinal cord, and wherein the direct current stimulation applied by the first electrode causes neural stem cells at or proximate to the dorsal aspect of the spinal cord to migrate toward the spinal cord condition at the spinal location.

2. The method of claim 1, wherein the second electrode is placed at a position remote from the dorsal aspect of the spinal cord, and wherein the first and second electrodes are oppositely charged.

3. The method of claim 2, wherein the first electrode is placed at or proximate to the spinal location, wherein the constant direct current causes neural cells at or proximate to the spinal location to at least one of migrate, proliferate and differentiate.

4. The method of claim 2, wherein the first electrode is a negatively charged electrode.

5. The method of claim 4, wherein the spinal cord condition is a spinal cord injury and wherein the constant direct current causes neural cells at the spinal cord to migrate toward the spinal cord injury at the spinal location.

6. The method of claim 4, wherein the constant direct current causes neural cells at or proximate to the spinal location to differentially express at least one member of the group consisting of BDNF, NGF and HSP70.

7. The method of claim 3, further including the step of injecting neural stem cells into the vertebrate being at or proximate to the spinal location.

8. The method of claim 7, wherein the constant direct current causes the injected neural stem cells to at least one of migrate, differentiate and proliferate relative to the spinal location.

9. The method of claim 8, wherein the first electrode is a positively charged electrode.

10. The method of claim 8, wherein the constant direct current causes the injected neural stem cells to migrate relative to the spinal location.

11. The method of claim 10, wherein the constant direct current causes the injected neural stem cells to differentially express at least one member of the group consisting of BDNF, NGF and HSP70.

12. The method of claim 2, wherein the constant direct current is provided having artifacts of at least one of constant, pulsed, varying, continuous, and intermittent direct current.

13. The method of claim 2, wherein at least one of the first and second electrodes is located at one or more of on a skin surface, subcutaneously, epidurally and subdurally.

14. The method of claim 2, wherein the spinal cord condition is associated with at least one member of the group consisting of post-traumatic compression or disruption by fractured or displaced vertebra, disk herniation, cervical spondylosis, arteriovenous malformation, hemorrhage, multiple sclerosis, neuromyelitis optica, tranverse myelitis, Sjogren-related myelopathy, systemic lupus erythematosus, syringomyelia, meningomyelocele, tethered cord syndrome, vitamin B12 deficiency, amyotrophic lateral sclerosis, hereditary spastic paraparesis, spinal muscular atrophy and tropical spastic paraparesis/HTLV-1-associated myelopathy.

15. The method of claim 2, wherein the direct current is held constant by varying voltage between the first and second electrodes in response to physiological changes of the vertebrate being.

16. The method of claim 2, wherein the first electrode is positively charged.

17. The method of claim 16, wherein the spinal cord condition is a spinal cord injury and wherein the constant direct current causes neural cells at the spinal cord to migrate relative to the spinal cord injury.

18. The method of claim 5, wherein the spinal cord injury is remote from the first electrode.

19. The method of claim 17, wherein the spinal cord injury is remote from the first electrode.

20. The method of claim 19, wherein the constant direct current causes neural cells at or proximate to the spinal cord injury to at least one of proliferate, differentiate and migrate.

21. The method of claim 19, wherein the constant direct current causes neural cells at or proximate to the spinal cord injury to differentially express at least one member of the group consisting of BDNF, NGF and HSP70.

22. The method of claim 5, further including the step of injecting neural stem cells into the vertebrate being at or proximate to the spinal cord injury.

23. The method of claim 17, further including the step of injecting neural stem cells into the vertebrate being at or proximate to the spinal cord injury.

24. The method of claim 3, further including the step of providing a DC power source having first and second terminals for energizing the first and second electrodes, including the step of providing a control circuit in electrical communication with at least one of the first and second electrodes and the power source, the control circuit configured to maintain constant current flow between the first and second electrodes in response to changes in voltage across the first and second terminals.

25. The method of claim 3, including the step of alternating a direction of the constant direct current.

26. The method of claim 1 further comprising the steps of:
a. providing a constant direct current source having a plurality of terminals;
b. providing a first terminal of the plurality of terminals for connecting the first electrode to the direct current source; and
c. providing a second terminal of the plurality of terminals for connecting a second electrode to the direct current source.

27. The method of claim 26 further including the step of providing a circuit to control a direction of current flow between the first electrode and the second electrode.

28. The method of claim 26 further comprising the step of providing a control circuit in electrical communication with at least one of the first and second electrodes and the direct current source, the control circuit maintaining constant current flow between the first and second electrodes in response to changes in voltage across the first and second terminals.

29. The method of claim 26, wherein the direct current source is a battery, and further comprising the step of providing a stimulation system in a housing configured for supporting the direct current source and the first and second terminals in the housing.

30. The method of claim 29, wherein the housing is wearable and configured to be secured to the vertebrate being and to permit the vertebrate being to be mobile while the system is in operation.

31. The method of claim 30, wherein a surface of the housing is configured for presenting the first electrode as an electrode surface of the housing for attachment directly to the vertebrate being in the dorsal aspect.

\* \* \* \* \*